(12) United States Patent
Frost

(10) Patent No.: US 7,790,431 B2
(45) Date of Patent: Sep. 7, 2010

(54) METHODS AND MATERIALS FOR THE PRODUCTION OF SHIKIMIC ACID

(75) Inventor: John W. Frost, Okemos, MI (US)

(73) Assignee: Board of Trustees Operating Michigan State University, East Lansing, MI (US)

(*) Notice: Subject to any disclaimer, the term of this patent is extended or adjusted under 35 U.S.C. 154(b) by 539 days.

(21) Appl. No.: 10/572,976

(22) PCT Filed: Sep. 24, 2004

(86) PCT No.: PCT/US2004/031417
§ 371 (c)(1),
(2), (4) Date: Nov. 20, 2006

(87) PCT Pub. No.: WO2005/030949
PCT Pub. Date: Apr. 7, 2005

(65) Prior Publication Data
US 2007/0087424 A1    Apr. 19, 2007

Related U.S. Application Data

(60) Provisional application No. 60/505,658, filed on Sep. 24, 2003.

(51) Int. Cl.
*C12N 9/88* (2006.01)
(52) U.S. Cl. ...................... 435/232; 435/108
(58) Field of Classification Search .................. 435/108, 435/232
See application file for complete search history.

(56) References Cited

U.S. PATENT DOCUMENTS

| | | |
|---|---|---|
| 5,164,382 A | 11/1992 | Sutherland et al. |
| 5,168,056 A | 12/1992 | Frost |
| 5,272,073 A | 12/1993 | Frost et al. |
| 5,629,181 A | 5/1997 | Frost et al. |
| 5,798,236 A | 8/1998 | Frost et al. |
| 5,821,266 A | 10/1998 | Frost |
| 5,906,925 A | 5/1999 | Liao |
| 6,436,664 B1 | 8/2002 | Lomantas et al. |
| 6,472,169 B1 | 10/2002 | Frost et al. |
| 6,613,552 B1 | 9/2003 | Frost |

FOREIGN PATENT DOCUMENTS

| | | |
|---|---|---|
| WO | 94/14955 | 7/1994 |
| WO | 96/34961 | 11/1996 |
| WO | 98/18937 | 5/1998 |
| WO | 00/44923 | 8/2000 |

OTHER PUBLICATIONS

Henderson et al. [J. org. Chem. (1998), vol. 63, pp. 906-907.*
Database EMBL 'Online! EBI; Oct. 1, 2002, "4-Hydroxy-2-oxoglutarate aldolase/2-dehydro-3-deoxyphosphogluconate aldolase (dgoA)": XP002317419 retrieved from EMBL accession No. Q8PLM9 (see sequence).

Da Silva A C R et al: "Comparison of the genomes of two *Xanthomonas* pathogens with differing host specificities" NATURE (London), vol. 417, No. 6887, May 23, 2002, pp. 459-463, XP002317414; ISSN: 0028-0836.
Database EMBL 'Online! EBI; Oct. 1, 2002, "4-Hydroxy-2-Oxogluterate Aldolase/2-Deydro-3-Deoxyphosphogluconate Aldolase": XP002317420 retrieved from EMBL accession No. Q8P9V0 (see sequence).
Database EMBL 'Online! EBI: Mar. 1, 2003, "2-dehydro-3-deoxyphosphogal actonate aldolase, putative": XP002317421, retrieved from EMBL accession No. Q8FVA7 (see sequence).
Paulsen Ian T et al: "The Brucella suis genome reveals fundamental similarities between animal and plant pathogens and symbionts" Proceedings of the National Academy of Sciences of the United States of America, vol. 99, No. 20, Oct. 1, 2002, pp. 13148-13153, XP002317415; ISSN: 0027-8424.

(Continued)

*Primary Examiner*—Tekchand Saidha
(74) *Attorney, Agent, or Firm*—Jennifer A. Camacho; Greenberg Traurig LLP

(57) ABSTRACT

Novel enzymes and novel enzymatic pathways for the pyruvate-based synthesis of shikimate or at least one intermediate thereto or derivative thereof, nucleic acids encoding the enzymes, cells transformed therewith, and kits containing said enzymes, cells, or nucleic acid. A KDPGal aldolase is used to perform condensation of pyruvate with D-erythrose 4-phosphate to form 3-deoxy-D-arabino-heptulosonate-7-phosphate (DAHP); a 3-dehydroquinate synthase is used to convert the DAHP to 3-dehydroquinate (DHQ); DHQ dehydratase can then convert DHQ to the key shikimate intermediate, 3-dehydroshikimate.

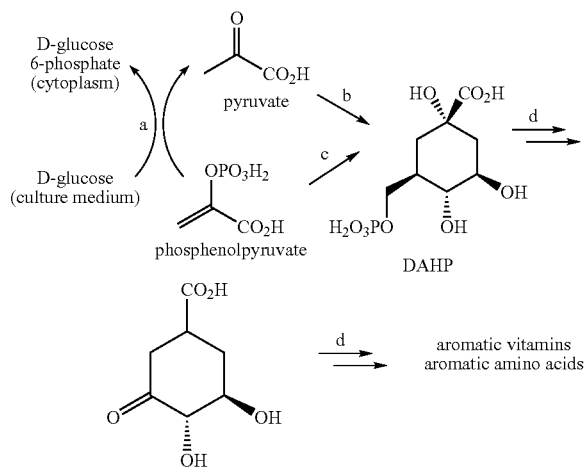

a) carbohydrate phosphotransferase; (b) KDPGal aldolase, D-erythrose 4-phosphate; (c) DAHP synthase, D-erythrose 4-phosphate; (d) shikimate pathway enzymes

19 Claims, 5 Drawing Sheets

OTHER PUBLICATIONS

Database EMBL 'Online! EBI; Mar. 1, 2002, "Putative 2-dehydro-3deoxyphosphogalactonate aldolase protein (EC 4.1.2.21)"; XP002317422, retrieved from EMBL accession No. Q8XVS7 (see sequence).

Salanoubat M et al: "Genome sequence of the plant pathogen *Ralstonia solanacearum*", Nature (London), vol. 415, No. 6871, Jan. 31, 2002, pp. 497-502, XP002317416; ISSN: 0028-0836.

Ran Ninqoing et al: "Creation of a shikimate pathway variant." Journal of the American Chemical Society. Jun 9, 2004, vol. 126, No. 22, Jun. 9, 2004, pp. 6856-6857, XP002317417; ISSN: 0002-7863.

Knaggs A R: "The biosynthesis of shikimate metabolites." Natural Product Reports. Jun. 2001, vol. 18, No. 3, Jun. 2001, pp. 334-355, XP002317418; ISSN: 0265-0568.

International Search Report and Written Opinion of ISA for PCT/US2004/031417, dated Feb. 11, 2005; ISA/EPO.

Arias, A., et al., "Galactose Metabolism in *Rhizobium meliloti* L5-30," Journal of Bacteriology, vol. 167, No. 3, pp. 1092-1094, (1986).

Attwood, T., Science Magazine, "Genomics: The Babel of Bioinformatics," vol. 290, No. 5491, pp. 471-173, (2000).

Brown, K.D., et al., "Transport and Utilization of the Biosynthetic Intermediate Shikimic Acid in *Escherichia Coli*," Biochimica et Biophysica Acta, vol. 428, pp. 550-562, (1976).

Crameri, A., et al., "DNA shuffling of a family of genes from diverse species accelerates directed evolution," Nature, vol. 391, pp. 288-291, (1998).

Datsenko, K.A., et al., "One-step inactivation of chromosomal genes in *Escherichia coli* K-12 using PCR products," Proceedings of the National Academy of Sciences of the United States of America, vol. 97, No. 12, pp. 6640-6645, (2000).

Dell, K.A., et al., "Identification and Removal of Impediments to Biocatalytic Synthesis of Aromatics From D-Glucose: Rate-Limiting Enzymes in the Common Pathway of Aromatic Amino Acid Biosynthesis," Journal of American Chemical Society, vol. 115, pp. 11581-11589, (1993).

Draths, K.M., et al., "Biocatalysis and Nineteenth Century Organic Chemistry: Conversion of D-Glucose Into Quinoid Organics," Journal of American Chemical Society, vol. 114, No. 24, pp. 9725-9726, (1992).

Draths, K.M., et al., "Environmentally Compatible Synthesis of Catechol From D-Glucose," Journal of American Chemical Society, vol. 117, pp. 2395-2400, (1995).

Draths, K.M., et al., "Shikimic acid and Quinic Acid: Replacing Isolation from Plant Sources with Recombinant Microbial Biocatalysis," Journal of American Chemical Society, vol. 121, No. 7, pp. 1603-1604, (1999).

Frost, J. et al., "Biocatalytic Syntheses of Aromatics From D-Glucose: Renewable Microbial Sources of Aromatic Compounds," Annual Review of Microbiology, vol. 49, pp. 557-579, (1995).

Frost, et al., "Dehydroquinate Synthase from *Escherichia coli*: Purification, Cloning, and Construction of Overproducers of the Enzyme. Biochemistry," vol. 23, pp. 4470-4475, (1984).

Gu, W., et al., "Imidazole Acetol Phosphate Aminotransferase in Zymomonas Mobilis: Molecular Genetic, Biochemical, and Evolutionary Analyses," Journal of Bacteriology, vol. 177, pp. 1576-1584, (1995).

Haslam, Edwin, "Chemistry of Intermediates in the Common Pathway," Shikimic Acid: Metabolism and Metabolites, John Wiley & Sons, New York, pp. 40-42, (1993).

Kikuchi, et al., "Mutational Analysis of the Feedback Sites of Phenylalanine-Sensitive 3-Deoxy-D-Arabino-Heptulosonate-7-Phosphate Synthase of *Escherichia coli*," Applied and Environmental Microbiology, vol. 63, No. 2, pp. 761-762, (1997).

Kim, C.U., et al., "Influenza Neuraminidase Inhibitors Possessing a Novel Hydrophobic Interaction in the Enzyme Active Site: Design, Synthesis, and Structural Analysis of Carbocyclic Sialic Acid Analogues With Potent Anti-Influenza Activity," Journal of American Chemical Society, vol. 119, No. 4, pp. 681-690, (1997).

Knop, David R., et al., "Hydroaromatic Equilibration During Biosynthesis of Shikimic Acid," Journal of American Chemical Society, vol. 123, No. 42, pp. 10173-10182, (2001).

Konstantinov, K.B., et al., "Glucose Feeding Strategy Accounting for the Decreasing Oxidative Capacity of Recombinant *Escherichia coli* in Fed-Batch Cultivation for Phenylalamine Production," Journal of Fermentation and Bioengineering, vol. 70, No. 4, pp. 253-260, (1990).

Konstantinov, K.B., et al., "Physiologically Motivated Strategies for Control of the Fed-Batch Cultivation of Recombinant *Escherichia coli* for Phenylalanine Production," Journal of Fermentation and Bioengineering, vol. 71, No. 5, pp. 350-355, (1991).

Kurn, N., et al., "Galactose Catabolism in *Caulobacter crescentus*," Journal of Bacteriology, vol. 135, No. 2, pp. 517-520, (1978).

Li, Kai, et al., "Utilizing Succinic Acid as a Glucose Adjunct in Fed-Batch Fermentation: Is Butane a Feedstock Option in Microbe-Catalyzed Synthesis?," Journal of American Chemical Society, vol. 121, No. 40, pp. 9461-9462, (1999).

Mitsuhashi, S., et al., "Aromatic Biosynthesis—XIII. Conversion of Quinic Acid to 5-Dehydroquinic Acid by Quinic Dehydrogenase," Biochimica Biophysica Acta, vol. 15, pp. 268-280, (1954).

Nierman, W.C., et al., "Complete genome sequence of *Caulobacter crescentus*," Proceedings of the National Academy of Sciences of the United States of America, vol. 98, pp. 4136-4141, (2001).

Patnaik, R., et al., "Engineering of *Escherichia Coli* Central Metabolism for Aromatic Metabolite Production With Near Theoretical Yield," Applied and Environmental Microbiology, vol. 60, No. 11, pp. 3903-3908, (1994).

Pittard, J., et al., "Gene Controlling the Uptake of Shikimic Acid by *Escherichia Coli*," Journal of Bacteriology., vol. 92, No. 4, pp. 1070-1075, (1966).

Rohloff, J.C. et al., "Practical Total Synthesis of the Anti-Influenza Drug GS-4104," The Journal of Organic Chemistry, vol. 63, No. 12, pp. 4545-4550, (1998).

Stouthammer, A.H., "Glucose and Galactose Metabolism in Gluconobacter Liquefaciens," Biochimica et Biophysica Acta, vol. 48, No. 3, pp. 484-500, (1981).

Szumilo, Tadeusz, "Pathway for D-Galactonate Catabolism in Nonpathogenic Mycobacteria," Journal of Bacteriology, vol. 148, No. 1, pp. 368-370, (1981).

Tan, D.S., et al., "Stereoselective Synthesis of Over Two Million Compounds Having Structural Features Both Reminiscent of Natural Products and Compatible With Miniaturized Cell-Based Assays," Journal of American Chemical Society, vol. 120, No. 33, pp. 8565-8566, (1998).

Weaver et al., "Cloning of an aroF Allele Encoding a Tyrosine-Insensitive 3-deoxy-d-Arabino-Heptulosonate 7-Phosphate Synthase," Journal of Bacteriology, vol. 172, No. 11, pp. 6581-6584, (1990).

Whipp, M.J., et al., "Cloning and Analysis of the shiA Gene, which Encodes the Shikimate Transport System of *Escherichia Coli* K-12," Gene, vol. 209, pp. 185-192, (1998).

Whipp, M.J., et al., "A Reassessment of the Relationship Between aroK- 1-47 and aroL-encoded Shikimate Kinase Enzymes of *Escherichia Coli*," Journal of Bacteriology, vol. 177, No. 6, pp. 1627-1629, (1995).

Wong, T.Y., et al., "The DeLey-Doudoroff Pathway of Galactose Metabolism in *Azobacter vinelandii*," Applied Environmental Microbiology, vol. 60, No. 6, pp. 2065-2068, (1994).

\* cited by examiner (a) carbohydrate phosphotransferase; (b) KDPGal aldolase, D-erythrose 4-phosphate;
(c) DAHP synthase, D-erythrose 4-phosphate; (d) shikimate pathway enzymes

Figure 3

| Plasmid (size) | Plasmid Map[a] |
|---|---|
| pNR5.223 (4.5-kb) | X — kan[R] → Ap[R] → X P[lac] EC dgoA → X |
| pNR7.088 (4.8-kb) | P — Ap[R] → B lacI[Q] ← P[trc] EC dgoA → P |
| pNR7.118 (5.9-kb) | P — Ap[R] → B lacI[Q] ← P[tac] EC dgoA → P |
| pNR6.252 (5.9-kb) | E — Ap[R] → E lacI[Q] ← P[tac] KP dgoA → E |
| pNR7.126 (6.4-kb) | B — Ap[R] → E lacI[Q] ← P[tac] aroF[FBR] → B |
| pNR7.288 (8.5-kb) | N N E (Bg) (Bg) E K (S) N — Ap[R] → P[lac] (aroF) cat (aroF) aroE serA → |
| pNR7.297 (5.2-kb) | B — Cm[R] → B P[lac] (aroG) ← (M) tet (M) → (aroG) → B |
| pNR7.290 (6.8-kb) | H — Ap[R] → lacI[Q] ← X P[trc] (aroH) → P Kan[R] ← P (aroH) H |
| pKP03-3 (5.9-kb) | E — Ap[R] → E lacI[Q] ← P[tac] KP03-3 → B |
| pEC03-1 (4.8-kb) | P — Ap[R] → B lacI[Q] ← P[trc] EC03-1 → P |
| pNR8.074 (7.5-kb) | (H) — Ap[R] → E E lacI[Q] ← P[tac] KP dgoA → serA ← (H) |
| pKP03-3serA (7.5-kb) | (H) — Ap[R] → E lacI[Q] ← B P[tac] KP03-3 → serA → (H) |
| pNR8.075 (6.8-kb) | (H) — Ap[R] → B lacI[Q] ← P P[trc] EC dgoA → serA ← (H) |
| pEC03-1serA (6.8-kb) | (H) — Ap[R] → B lacI[Q] ← P P[trc] EC03-1 → serA ← (H) |

METHODS AND MATERIALS FOR THE PRODUCTION OF SHIKIMIC ACID

CROSS REFERENCE TO RELATED APPLICATION

This application is the National Stage of International application PCT/US2004/031417 filed on Sep. 24, 2004, and published as WO 2005/030949 A1, which claims the benefit of U.S. Provisional Patent Application No. 60/505,658, filed on Sep. 24, 2003, now expired, each of the foregoing of which is incorporated by reference herein in its entirety.

This invention was made with Government support under Contract 08-R1GM065541A, awarded by the National Institutes of Health. The Government may have certain rights in this invention.

INTRODUCTION

The present invention relates to methods, materials and organisms for the production of shikimic acid and related compounds. In particular, such methods relate to microbial synthetic processes using pyruvate.

Shikimic acid is an attractive chiral compound useful in a variety of synthetic reaction. It has a highly functionalized, six-membered carbocyclic ring, and multiple asymmetric centers. A metabolic intermediate of aromatic amino acid biosynthesis, shikimic acid is a commercially valuable chiral starting material in the synthesis of neuraminidase inhibitors effective in the treatment of influenza. See, e.g., Kim. C. U. et al., *J. Am. Chem. Soc.* 119:681 (1997); and Rohloff, J. C. et al., *J. Org. Chem.* 63:4545 (1998). Chiral, as well as aromatic chemicals, can also be synthesized from shikimic acid. For example, acid catalyzed dehydration of shikimic acid affords p-hydroxybenzoic acid, which has an annual production of over seven million kilograms, and is the key precursor to parabens and a monomer used in the synthesis of liquid crystal polymers. Shikimic acid has also been used as the starting point for synthesis of a large combinatorial library of molecules. See, e.g., Tan, D. S. et al., *J. Am. Chem. Soc.* 120:8565 (1998).

Shikimic acid may be obtained via tedious multi-step isolation procedures from plants. Unfortunately, current isolation of shikimic acid from the fruit of *Illicium* plants (Haslem, E., "Shikimic Acid: Metabolism and Metabolites," Wiley & Sons, New York, pp. 40-42 (1993)) precludes its use in kilogram-level synthesis Microbial synthesis of shikimic acid is disclosed in U.S. Pat. No. 5,168,056, Frost, issued Dec. 1, 1992; U.S. Pat. No. 5,272,073, Frost et al., issued Dec. 21, 1993: U.S. Pat. No. 5,629,181, Frost et al., issued May 13, 1997; and U.S. Pat. No. 6,613,552, Frost et al., issued Sep. 2, 2003. Such methods employ variations on the common pathway for aromatic amino acid biosynthesis.

Phosphoenolpyruvate (PEP) is a substrate for the first committed step in the shikimate pathway (FIG. 1) and is also used by the carbohydrate phosphotransferase (PTS) system for microbial transport and phosphorylation of glucose. The resulting competition between the shikimate pathway and PTS-mediated glucose transport for cytoplasmic supplies of phosphoenolpyruvate limits the concentrations and yields of natural products microbially synthesized by way of the shikimate pathway.

SUMMARY

The present invention provides methods for producing shikimic acid comprising enzyme-catalyzed condensation of pyruvate with D-erythrose 4-phosphate to form 3-deoxy-D-arabino-heptulosonate 7-phosphate (DAHP). Also provided are methods for making shikimic acid, as depicted in FIG. 2, and transfected microbes expressing 2-keto-3-deoxy-6-phosphogalactonate (KDPGal) aldolase.

The present invention further provides:

Recombinant KDPGal aldolase polypeptides having the ability to catalyze the condensation of pyruvate and E4P to from DAHP, containing at least one mutation that is X10V, X28L or X28M, X42T, X85A, X154F, or X196I; KDPGal aldolase polypeptides containing at least one mutation that is I10V, V28L or V28M, S42T, V85A, V154F, or F196I;

KDPGal aldolase polypeptides having, apart from one of these mutations, the amino acid sequence of any one of SEQ ID NO:2, SEQ ID NO:4, and SEQ ID NO:6, or an amino acid sequence at least 50% homologous to one of these; recombinant KDPGal aldolase polypeptides whose amino acid sequences are variants of a native KDPGal aldolase amino acid sequence;

Nucleic acid encoding such a recombinant KDPGal aldolase polypeptide; vectors containing such nucleic acid;

Enzymatic pathways capable of converting pyruvate and D-erythrose 4-phosphate (E4P) into 3-deoxy-D-arabino-heptulosonate-7-phosphate (DAHP), by virtue of their having at least one KDPGal aldolase; such enzymatic pathways also capable of converting DAHP to DHQ by virtue of their having at least one DHQ synthase, and optionally at least one DHQ dehydratase, and further optionally at least one shikimate dehydrogenase;

Methods for the production of shikimate or a shikimate intermediate, such as DAHP, DHQ, or DHS, by growing a recombinant host cell containing nucleic acid encoding at least one KDPGal aldolase and at least one DHQ synthase, such that the cell expresses those enzymes. Methods for converting pyruvate and E4P to DAHP or a derivative of DAHP in vitro or in vivo/in cyto;

The use of a recombinant KDPGal aldolase to produce DAHP from pyruvate and E4P; the use of a combination of recombinant KDPGal aldolase and DHQ synthase to produce DHQ.

Process for preparing recombinant cells capable of expressing a KDPGal aldolase, and thus of converting pyruvate and E4P to DAHP by providing a host cell capable of synthesizing pyruvate and E4P, providing a vector containing a polynucleotide from which said host cell can express a KDPGal aldolase, and transforming said cell with said vector to produce a transformed cell, and, optionally, expressing the KDPGal aldolase, whereupon the cell converts pyruvate and E4P to DAHP. Recombinant cells prepared thereby;

Processes for preparing DAHP or a derivative thereof, by providing (A) a supply of E4P and pyruvate, (B) a KDPGal aldolase, and optionally a DHQ synthase, (C) an aqueous medium; contacting the KDPGal aldolase with the E4P and pyruvate under conditions in which the KDPGal aldolase can catalyze the formation of DAHP therefrom, and optionally contacting the DAHP with the DHQ synthase under conditions in which the DHQ synthase can catalyze the formation of 3-dehydroquinate from the DAHP; and optionally recovering at least one of DAHP, DHQ, DHS, or a further-derivative thereof;

In vivo embodiments of such methods, pathways, and cells further including a recombinant transketolase or a recombinant transaldolase;

Kits containing a KDPGal aldolase preparation, with instructions for the use thereof to convert pyruvate and E4P to DAHP, and optionally with instructions for the conversion of said DAHP to at least one derivative thereof;

Kits containing a cell capable of expressing a KDPGal aldolase, with instructions for the use thereof to convert pyruvate and E4P to DAHP, and optionally with instructions for the conversion of said DAHP to at least one derivative thereof;

Kits containing nucleic acid from which a cell can express at least one KDPGal aldolase, with instructions for the use thereof to transform a cell to produce a transformed cell that is capable of converting pyruvate and E4P to DAHP, and optionally to at least one derivative thereof.

FIGURES

FIG. 3 sets forth restriction enzyme maps for plasmids useful in the methods of this invention.

Figure 4:
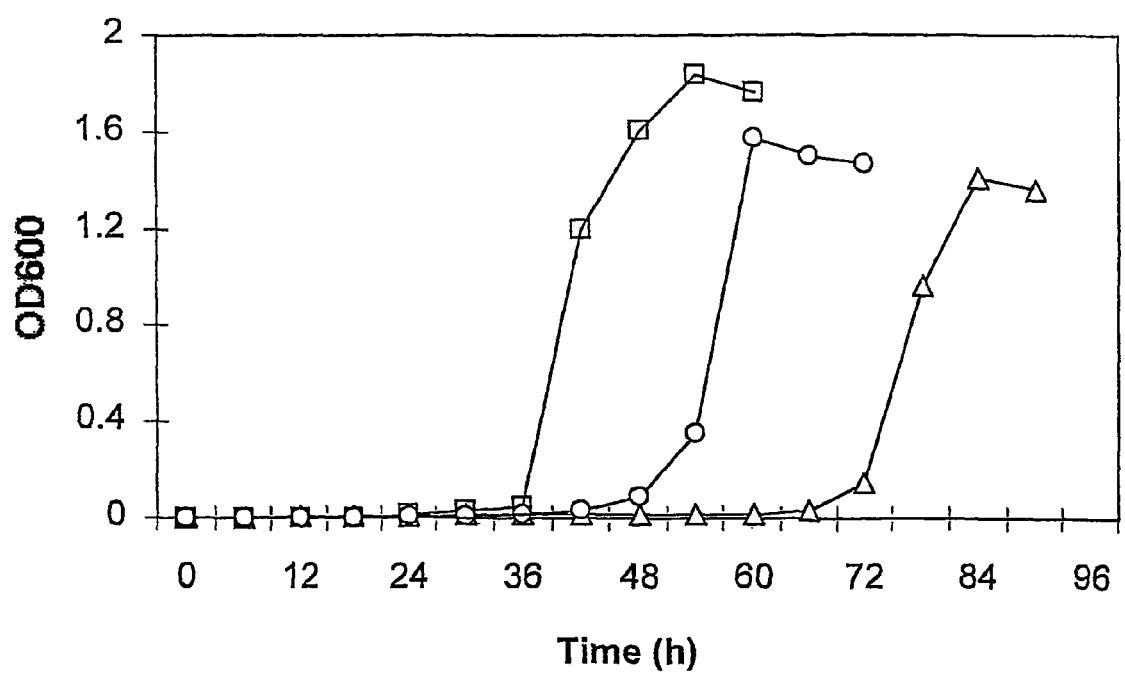

FIG. 4 is a plot depicting showing the growth of organisms among those useful herein.

Figure 5:
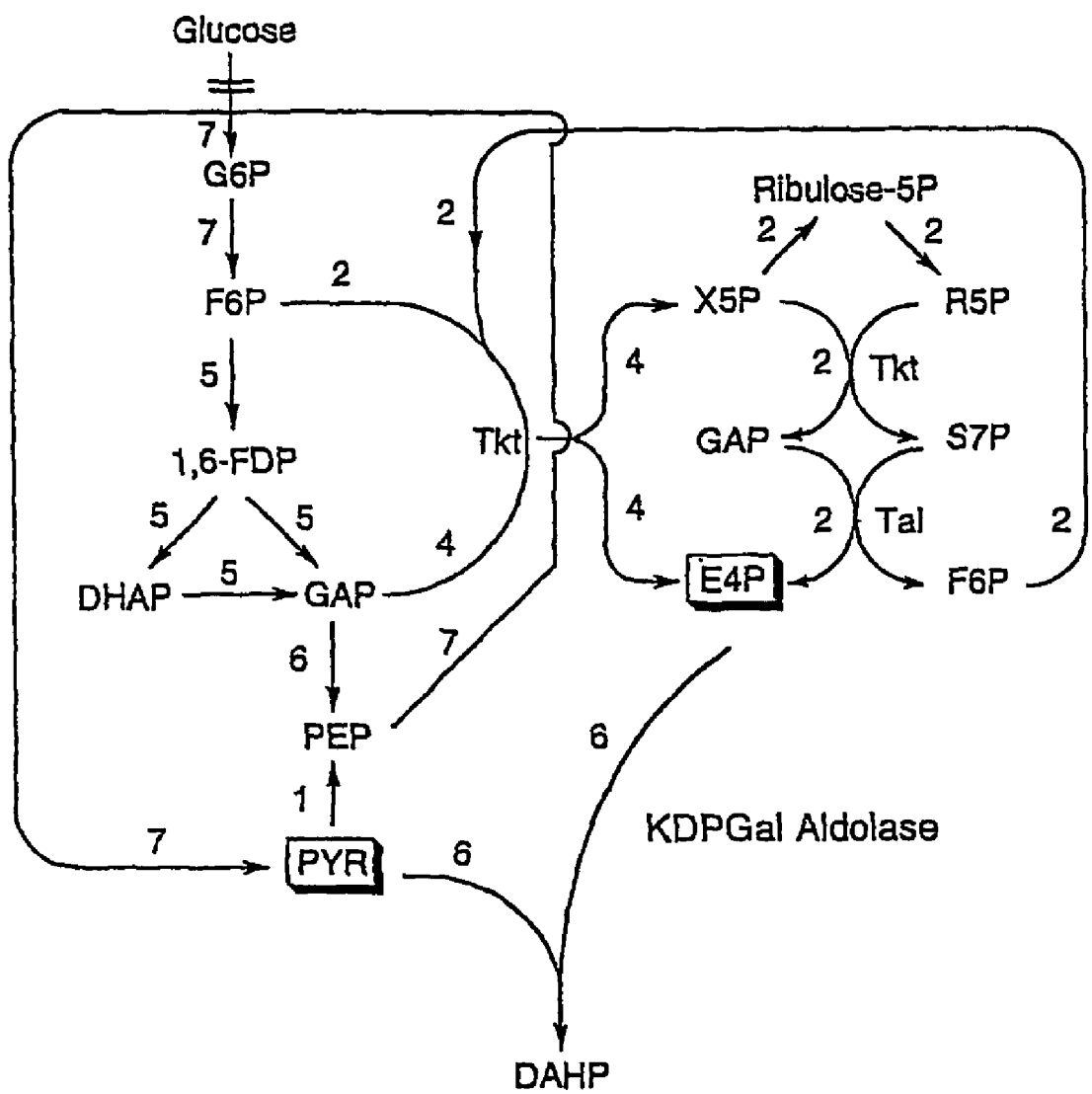

FIG. 5 depicts a synthetic scheme for enhanced conversion of glucose to DAHP via a pyruvate-based pathway according to the present invention. The numbers are the relative fluxes involved in converting 7 mol of glucose into DAHP. Enzymes are: Pps, PEP synthase; Tkt, transketolase; Tal, transaldolase. Metabolites are: G6P, glucose 6-phosphate; F6P, fructose 6-phosphate; 1,6-FDP, 1,6-fructose diphosphate; DHAP, dihydroxyacetone phosphate; GAP, glyceraldehyde 3-phosphate; R5P: ribose 5-phosphate; X5P, xylulose 5-phosphate; S7P, sedoheptulose 7-phosphate; PYR, pyruvate. This scheme shows that E4P production can be improved by enhancing expression of Tkt and/or Tal, thereby increasing the synthesis of DAHP by KDPGal aldolase.

It should be noted that the figures set forth herein are intended to exemplify the general characteristics of an apparatus, materials and methods among those of this invention, for the purpose of the description of such embodiments herein. These figures may not precisely reflect the characteristics of any given embodiment, and are not necessarily intended to define or limit specific embodiments within the scope of this invention.

DESCRIPTION

The present invention provides methods, materials and organisms for producing shikimic acid and intermediates. The following definitions and non-limiting guidelines must be considered in reviewing the description of this invention set forth herein.

The headings (such as "Introduction" and "Summary,") and sub-headings used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

The word :"recombinant" is used herein to indicate that nucleic acid manipulation was employed. As a result, phrases such as "recombinant" nucleic acid, "recombinant" polypeptide, and "recombinant" cell to entities that were produced, at least in part, by nucleic acid manipulation.

Sequence Homology

In a preferred embodiment, a mutant polypeptide according to the present invention will have an amino acid sequence that is at least 50% homologous to that of a native polypeptide performing the same function as the mutant. By way of example, a KDPGal aldolase according to the present invention will have an amino acid sequence at least 50% homologous to that of any of SEQ ID NO:2, SEQ ID NO:4, and SEQ ID NO:6; in a preferred embodiment, the sequence will be at least 60% homologous thereto; in a preferred embodiment, the sequence will be at least 70% homologous thereto; in a preferred embodiment, the sequence will be at least 80% homologous thereto; in a preferred embodiment, the sequence will be at least 90% homologous thereto.

In one embodiment, a recombinant polynucleotide according to the present invention, which encodes a desired polypeptide, will be any that encodes a polypeptide having homology to a native polypeptide of the same function, as described above. In one embodiment, a recombinant polynucleotide according to the present invention, which encodes a desired polypeptide, will have an amino acid sequence that is more than 80% homologous to that of a native polynucleotide encoding a polypeptide performing the same function as the mutant. In a preferred embodiment, the polynucleotide will be at least 85% homologous thereto; in a preferred embodiment, the polynucleotide will be at least 90% homologous thereto; in a preferred embodiment, the polynucleotide will be at least 95% homologous thereto.

Sequence homology refers to the degree of identicality between two sequences of amino acid residues, or between two sequences of nucleobases. This may be determined by visual comparison of two sequences, or by use of bioinformatic algorithms that align sequences for comparison or that determine percent homology among compared sequences. Useful automated algorithms are available in the GAP, BEST- FIT, FASTA, and TFASTA computer software modules of the Wisconsin Genetics Software Package (available from Genetics Computer Group, Madison, Wis., USA). The alignment algorithms automated in those modules include the Needleman & Wunsch, the Pearson & Lipman, and the Smith & Waterman sequence alignment algorithms. Other useful algorithms for sequence alignment and homology determination are automated in software including: FASTP, BLAST, BLAST2, PSIBLAST, and CLUSTAL V; see, e.g., N. P. Brown et al., *Bioinformatics*: Applications Note, 1998, 14:380-81; the U.S. National Center for Biotechnology Information at http://www.ncbi.nlm.nih.gov/Tools/index.html; and U.S. Pat. No. 6,790,639, which provides software parameter settings useful for homology determination herein.

The sequence homology exhibited by nucleobase polymers, such as nucleic acids and nucleic acid analogs, may be determined by hybridization assays between a first sequence and the complement of a second sequence. Any of the well known hybridization assays may be used for this purpose, and examples of these include those described in U.S. Pat. Nos. 6,767,744, and 6,783,758, with "high stringency" hybridization conditions being as defined therein.

Conservative Substitutions

In addition, conservative amino acid substitutions may be present in a polypeptide according to the present invention. The term "conservative amino acid substitution" indicates any amino acid substitution for a given amino acid residue, where the substitute residue is so chemically similar to that of the given residue that no substantial decrease in polypeptide function (e.g., enzymatic activity) results. Conservative amino acid substitutions are commonly known in the art and examples thereof are described, e.g., in U.S. Pat. Nos. 6,790, 639, 6,774,107, 6,194,167, or 5,350,576. In a preferred embodiment, a conservative amino acid substitution will be any one that occurs within one of the following six groups 1. Small aliphatic, substantially non-polar residues: Ala, Gly, Pro, Ser, and Thr;
2. Large aliphatic, non-polar residues: Ile, Leu, and Val; Met;
3. Polar, negatively charged residues and their amides: Asp and Glu;
4. Amides of polar, negatively charged residues: Asn and Gin; His;
5. Polar, positively charged residues: Arg and Lys; His; and
6. Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gln; His); Asp (Glu); Gin (Asn); Glu (Asp); Gly (Pro); His (Asn; Gin); Ile (Leu; Val); Leu (Ile; Val); Lys (Arg; Gin; Glu); Met (Leu; Ile); Phe (Met; Leu; Tyr); Ser (Thr); Thr (Ser); Trp (Tyr); Tyr (Trp; Phe); and Val (Ile; Leu).

Just as a polypeptide may contain conservative amino acid substitution(s), a polynucleotide hereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, e.g., a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

Production of Shikimate and its Precursors

Figure 1:
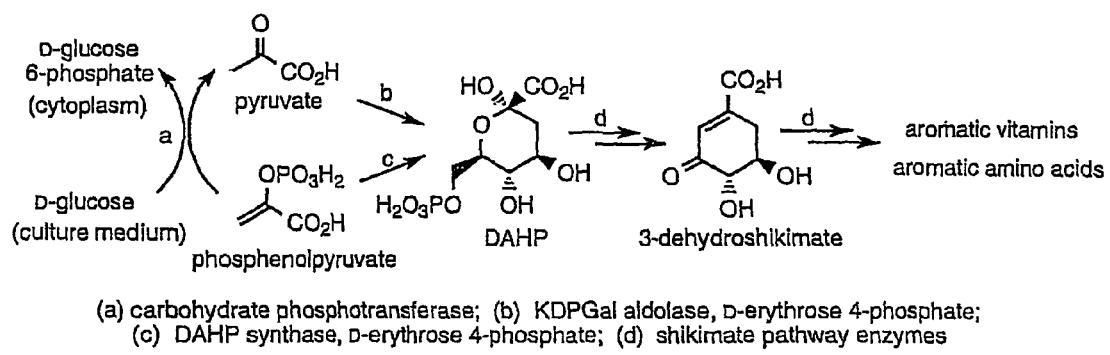
FIG. 1 depicts a synthetic scheme for 3-dehydroshikimate.
Figure 2:
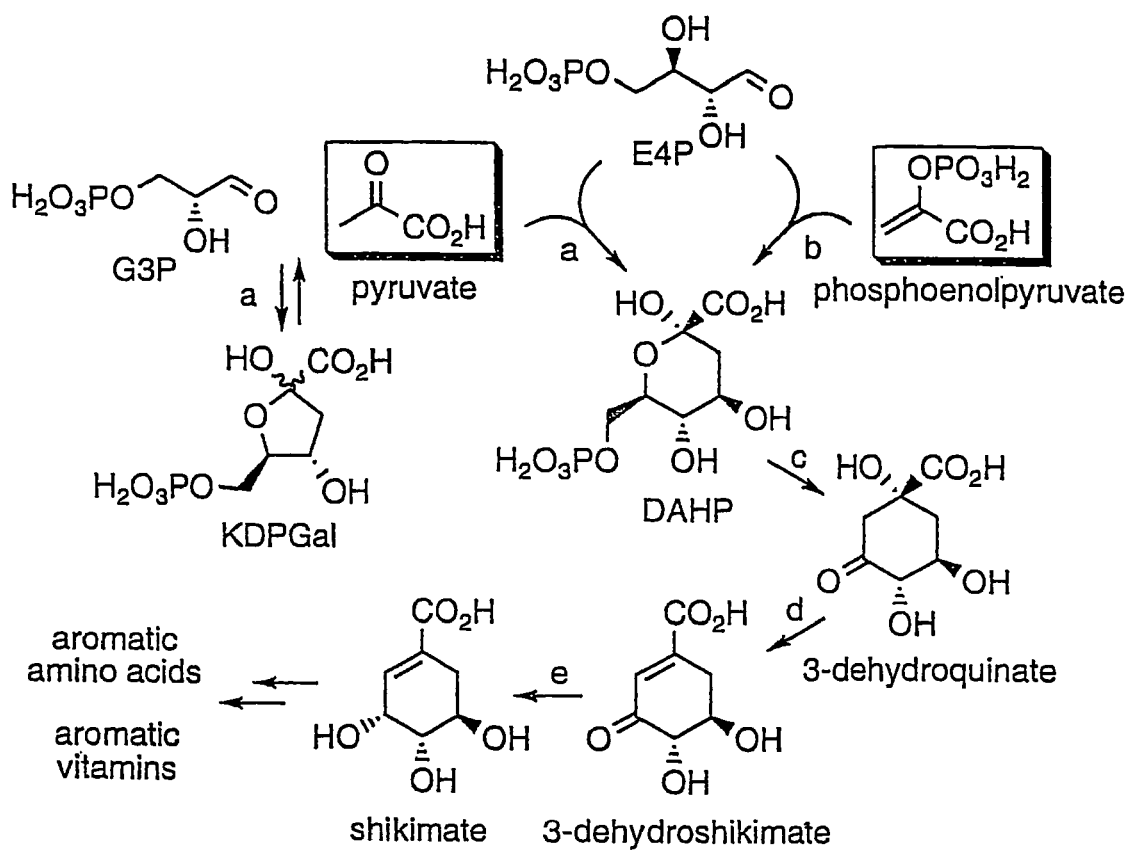
FIG. 2 depicts a synthetic scheme for shikimic acid and intermediate compounds.

In various embodiments, methods of this invention comprise the production of shikimate and shikimic acid according to the reaction schemes set forth in FIG. 2. As referred to in FIG. 2, "G3P" is D-glyceraldehyde 3-phosphate; "E4P" is D-erythrose 4-phosphate; "KDPGal" is 2-keto-3-deoxy-6-phosphogalactonate; "DAHP" is 3-deoxy-D-arabino-heptulosonate-7-phosphate. The enzymes used in the depicted method are (a) KDPGal aldolase (DgoA; also called 2-dehydro-3-deoxy-6-phosphogalactonate aldolase; E.C. 4.1.2.21); (b) DAHP synthase (AroF, AroG, AroH); (c) 3-dehydroquinate synthase (AroB); (d) 3-dehydroquinate dehydratase (AroD); and (e) shikimate dehydrogenase (AroE). In other embodiments, methods of this invention comprise the production of at least one of DAHP, DHQ (3-dehydroquinate), or DHS (3-dehydroshikimate).

By catalyzing the reversible cleavage of KDPGal to pyruvate and D-glyceraldehyde 3-phosphate (G3P, FIG. 2), KDPGal aldolase enables microbes (e.g.,*E. coli*) to use D-galactonate as a sole carbon source. In one embodiment,*E. coli* dgoA-encoded KDPGal aldolase is overexpressed, partially purified, and incubated with pyruvate, D-erythrose 4-phosphate (E4P), 3-dehydroquinate synthase, and 3-dehydroquinate dehydratase to form 3-dehydroshikimate. Dehydratase-catalyzed dehydration of 3-dehydroquinate provides in product 3-dehydroshikimate a chromophore suitable for continuous spectrophotometric assay.

In one embodiment, KDPGal aldolase is incubated with pyruvate and D-erythrose 4-phosphate to form DAHP; in one embodiment, KDPGal aldolase is incubated with pyruvate, D-erythrose 4-phosphate, and 3-dehydroquinate synthase to form DHQ. In one embodiment, KDPGal is expressed in a cell that provides pyruvate and E4P; DAHP can be formed thereby. In one embodiment, KDPGal is expressed in a cell that provides pyruvate, E4P, and 3-dehydroquinate synthase; DHQ can be formed thereby.

Production systems according to the present invention may be in vivo systems or in vitro systems. In vitro systems include, e.g., batch enzyme suspensions or (adsorbed or covalently) immobilized enzyme bioreactors. In vivo systems include, e.g., immobilized cell bioreactors, continuous fermentations, and batch fermentations. A DAHP synthesis system according to the present invention will include at least one KDPGal aldolase (DgoA) and a source of pyruvate and E4P. A DHQ synthesis system according to the present invention will include at least at least one KDPGal aldolase, a source of pyruvate and E4P, and at least one DHQ synthase (AroB). A DHQ synthase-containing enzymatic pathway or production system according to the present invention offers the additional benefit that, in contrast to the reversible reaction forming DAHP from pyruvate and E4P, the reaction forming DHQ from DAHP is irreversible due to cleavage of the phosphate ester. This can result in increased yields of DHQ and downstream derivatives thereof, e.g., shikimate. The coding sequence of an exemplary aroB gene is the *E. coli* sequence (SEQ ID NO:7).

Recombinant host cells according to the present invention are capable of expressing at least one recombinant KDPGal aldolase and optionally at least one DHQ synthase or other shikimate pathway enzyme. In a preferred embodiment, the recombinant cell capable of expressing KDPGal aldolase, and optionally of expressing DHQ synthase, will be a walled cell. Examples of walled cells include plant cells, yeast/fungal cells, bacterial cells, Archaea cells, and some protests. In a preferred embodiment, the recombinant cell will be a prokaryotic cell. In a preferred embodiment, the recombinant cell will be a bacterial cell. In a preferred embodiment, the recombinant cell will be a proteobacterial cell. Preferably, the recombinant host cell will lack the ability to express a functional DAHP synthase. In a preferred embodiment, the cell will be an aroFGH⁻ cell.

A DHS synthesis system according to the present invention will include at least at least one KDPGal aldolase, a source of pyruvate and E4P, at least one DHQ synthase, and at least one 3-dehydroquinate dehydratase. A shikimate synthesis system according to the present invention will include at least at least one KDPGal aldolase, a source of pyruvate and E4P, at least one DHQ synthase, at least one 3-dehydroquinate dehydratase, and at least one shikimate dehydrogenase.

EXAMPLES

Materials and Methods

Cloning, Plasmid Construction, Host Cells, and Transformation

Standard protocols can be used for construction, purification, and analysis of plasmid DNA. See, e.g., Sambrook, J.; Fritsch, E. F.; Maniatis, T., "Molecular Cloning—A Laboratory Manual," Cold Spring Harbor Laboratory: Plainview, N.Y., 1990. In various embodiments, *Escherichia coli* strain DH5α serve as the host strain for all plasmids constructions. *Klebsiella pneumoniae* genomic DNA can be purchased from the American Type Culture Collection (ATCC 700721D). *E. coli* strain CB734 [C600 leu thi1 Δ(gal-aroG-nadA)50 aroF:: cat(Cm$^R$) ΔaroH::Kan$^R$ recA1] may be obtained from Professor Ronald Bauerle (University of Virginia). *E. coli* strain JC7623, BW25141/pKD3 and BW25141/pKD46 may be obtained from the *E. coli* genetic stock center at Yale University. See, e.g., Lloyd, R. G.; Buckman, C., *J. Bacteriol.* 1985, 164, 836-844; and. Datsenko, K. A.; Wanner, B. L., *Proc. Natl. Acad. Sci. USA* 2000, 97, 6640-6645. Taq polymerase, large fragment of DNA polymerase I, calf intestinal alkaline phosphotase and pCR2.1-TOPO vector can be purchased from Invitrogen, Pfu polymerase was purchased from Strategene. DNaseI can be purchased from Roche Diagnostics. L-lactic dehydrogenase was purchased from Sigma. DNA clean and concentrator kit can be purchased from Zymo Research (Orange, Calif.). Phage P1 transduction, transformation with CaCl$_2$ and PCR amplifications can be performed by standard methods. *E. coli* genomic DNA can be purified as previously described. See, e.g., Pitcher, D. G.; Saunders, N. A.; Owen, R. J. *Lett. Appl. Microbiol.* 1989, 8, 151-156. *E. coli* strains W31105, AB32486, and KL37 and cloning vectors pJF118EH8 and pTrc99A9 can be obtained from the laboratory of Dr. John Frost, Michigan State University.

*Escherichia coli* dgoA gene sequences can be obtained from the National Center for Biotechnology Information (NCBI). See, e.g., Babbitt, P. C.; Mrachko, G. T.; Hasson, M. S.; Huisman, G. W.; Kolter, R.; Ringe, D.; Petsko, G. A.; Kenyon, G. L.; Gerlt, J. A. *Science* 1995, 267, 1159-1161. *Klebsiella pneumoniae* dgoA gene sequence can be obtained from the Genome Sequencing Center at Washington University using BLAST search against *E. coli* dgoA gene sequence.

Restriction maps for plasmids among those useful herein are set forth in FIG. 3. Sites are abbreviated as follows: X=XbaI, B=BamHI, Bg=BglII, E=EcoRI, P=PstI, K=KpnI, M=MfeI, N=NcoI, S=SmaI. Parentheses indicate that the designated enzyme site has been eliminated. Lightface lines indicate vector DNA; Boldface lines indicate insert DNA.

pNR5.223:

The 0.6-kb fragment containing the *E. coli* dgoA gene and its ribosomal binding site are amplified from *E. coli* W3110 genomic DNA using Taq polymerase with the following pair of primers containing XbaI recognition sequences, JWF 430 5'-GCTCTAGATGCAGTGGCAAACTAAACT (SEQ ID NO:13) and JWF 449 3'-GAC TCTAGATCATTGCACTGCCTCTCGAT (SEQ ID NO:14). The PCR fragment is mixed with pCR2.1TOPO vector to afford the 4.5-kb plasmid pNR5.223.

pNR7.088:

The 0.6-kb fragment containing the *E. coli* dgoA gene and its ribosomal binding site was amplified from *E. coli* W3110 genomic DNA using Pfu polymerase with the following pair of primers, JWF 484 5'-GAC GGATCCTATAAGGAGCATCGCTCATG (SEQ ID NO:15), JWF 529 3'-GAAG CTGCAGTCATTGCACTGCCTCTCGAT (SEQ ID NO:16). The PCR primers were designed to include BamHI and PstI recognition sequences at the 5' and 3' ends, respectively of the dgoA gene. Localization of the amplified dgoA as a BamHI-PstI fragment into the corresponding sites of pTrc99A afforded the 4.8-kb plasmid pNR7.088.

pNR7.118:

The 0.6-kb *E. coli* dgoA locus is excised from pNR7.088 by BamHI and PstI double digestion. Ligation to pJF118EH affords plasmid pNR7.118 in which the *E. coli* dgoA locus was located downstream the tac promoter.

pNR6.252:

The 5.9-kb plasmid contains *K. pneumoniae* dgoA gene located behind the tac promoter of pJF118EH. The 0.6-kb dgoA gene with its ribosomal binding site is amplified from *Klebsiella pneumoniae* subsp. *pneumoniae* genomic DNA (ATCC 700721 D) using the following primers, JWF 501 5'-GACAGGMTAAGGAGCATCG (SEQ ID NO:17), and JWF 499 5'-GGAGGTAMCGGTACGTGGT (SEQ ID NO:18). The resulting PCR fragment is ligated into pCR2.1TOPO vector by TA TOPO cloning technique to afford pNR6.223B. The 0.6-kb locus is then excised from pNR6.223B by EcoRI digestion and ligated to the EcoRI site of pJF118EH to afford plasmid pNR6.252.

pNR7.126:

The 6.4-kb plasmid is constructed by ligating the aroF$^{FBR}$ ("aroF Feedback-Resistant") gene with its ribosomal binding site into the EcoRI site of pJF118EH. The aroF$^{FBR}$ fragment is amplified by PCR from pKD12.112 using the following primers containing EcoRI terminal recognition sequence, JWF541 5'-GGAATTCGCATAAACAGGATCGCCATCA (SEQ ID NO:19) and JWF542 5'-CT GGATCCTTAAGCCACGCGAGCCGT (SEQ ID NO:20). See Draths, K. M. et al., *J. Am. Chem. Soc.,* 1999, 121, 1603-04.

pNR7.288:

The 0.8-kb cat gene is excised from pSU18 by digestion with BamHI, then is inserted into the BglII site internal to the aroF$^{FBR}$ gene in pKD12.112 to produce plasmid pNR7.288.

pNR7.297:

The 1.3-kb fragment containing aroG gene is amplified from *E. coli* W3110 genomic DNA using the following primers containing BamHI terminal recognition sequence, JWF 610 5'-GTGGATCCTTAATCCGTTCATAGTGTMA (SEQ ID NO:21), and JWF 611, 5'-TG GGATCCATGAGAAAGCCGACTGCAA (SEQ ID NO:22). The PCR fragment is ligated into pSU18 vector to create pNR7.260. Ligation of a SspI/AvaI digested tet-encoding fragment of DNA obtained from plasmid vector pBR322 into the MfeI site internal to the aroG gene in pNR7.260 resulted in plasmid pNR7.297.

pNR7.290:

The 1.3-kb fragment containing aroH gene is amplified from *E. coli* W3110 genomic DNA using the following primers JWF-625, 5'-GTTCGTCAGTGCAGGATGGA (SEQ ID NO:23) and JWF-626, 5'-GTTCAGGCGTGAGTTTTCT-GCT (SEQ ID NO:24). The PCR product is initially cloned into plasmid vector pCR2.1-TOPO, then the fragment containing aroH is digested with HindIII/XbaI and inserted into the HindIII/XbaI site of plasmid pTrc99A to afford a 5.5-kb plasmid pNR7.289B. A 1.3-kb Kan$^R$ gene excised from plasmid pKAD62A by digestion of PstI is cloned into the PstI site internal to the aroH gene in pNR7.289B to yield plasmid pNR7.290.

pNR8.074:

The 1.6-kb serA gene is excised from plasmid pRC1.55B by SmaI digestion. Ligation of serA gene to plasmid pNR6.252 predigested with HindIII to afford the 7.5-kb plasmid pNR8.074.

pNR8.075:

The 1.6-kb serA gene is excised from plasmid pRC1.55B by SmaI digestion. Ligation of serA gene to plasmid pNR7.088 predigested with HindIII afforded the 6.8-kb plasmid pNR8.075.

Construction of aroFaroGaroH Triple Mutant Strain NR7:

Disruption of aroF, aroG and aroH genes in *E. coli* KL3 is done as follows. Plasmid pNR7.288 is digested with EcoRI to liberate the insertionally inactivated *E. coli* aroF gene. The purified fragment (aroF::cat) is electroporated into the hyper-recombinant *E. coli* strain JC7623. Chloroamphenicol resistant colonies are picked up from LB plate containing 20 μg/mL chloroamphenicol, and the genotype verified by size analysis of the DNA fragment amplified by PCR from chromosomal DNA using the following primers JWF-541, 5'-GGMTTCGCATAAACAGGATCGCCATCA (SEQ ID NO:25), and JWF-542, 5'-CTGGATCCTTAAGCCACGC-GAGCCGT (SEQ ID NO:26). The aroF::cat mutation is then transferred from JC7623aroF::cat to *E. coli* KL3 by phage P1-mediated transduction to prepare KL3aroF::cat.

Similarly, the fragment comprising aroH::Kan$^R$ is excised from plasmid pNR7.290 by digestion with XbaI and HindIII, then electroporated into JC7623. The JC7623aroH::Kan$^R$ mutants resulting from homologous recombination are resistant to 50 μg/mL kanamycin. The correct genotype is verified by PCR analysis from chromosomal DNA using the following primers JWF-636, 5'-TCCGTACTGCGCGTATTGAGA (SEQ ID NO:27) and JWF-637, 5'-AGAGGCGAGTTTTTC-GACCA (SEQ ID NO:28). P1 phage mediated transduction employed to transfer the aroH::Kan$^R$ mutation into KL3aroF::cat and produce NR3 [KL3aroF::cat aroH::Kan$^R$].

The aroG mutation is generated by the methods described by Datsenko and Wanner. See, Datsenko, K. A.; Wanner, B. L. *Proc. Natl. Acad. Sci. USA* 2000, 97, 6640-6645. Plasmid pNR7.297 is digested with KpnI and PstI to liberate a fragment containing aroG::tet cassette, the purified DNA is electroporated into NR3/pKD46 while expressing Red recombinase. Recombinants are selected for tetracycline resistance (5 μg/mL). Plasmid pKD46 are eliminated by growth at 42° C. Disruption of aroG is confirmed by PCR analysis using the following primers JWF-669, 5'-GCAGCATTGTGCCGC-CAGAA (SEQ ID NO:29) and JWF-670, 5'-GTGCGCTG-GTGAAATATCTT (SEQ ID NO:30). The KL3aroF::cat aroG::tet aroH::Kan$^R$ strain is designated herein as *E. coli* NR7.

Enzyme Assay

The cells are suspended in KH$_2$PO$_4$ (20 mM, pH 6.5) containing PMSF (1 Mm; phenyl methyl sulfonyl fluoride). Cell lysis is achieved by two passes through a French pressure cell (SLC Aminco) at 16000 psi (110.3 MPa). Cell debris is separated from lysate by centrifugation at 48000 g for 20 min at 4° C. Protein concentration is quantified using the Bradford dye-binding procedure with the assay solution purchased from Bio-Rad. See Bradford, M. M., *Anal. Biochem.*, 1976, 72, 248-54.

KDPGal Cleavage Assay

KDPGal aldolase activity is determined using a coupled enzyme assay previously described by Meloche: Meloche, H. P., Wood, W. A., *J. Biol. Chem.*, 1964, 239, 3515-18. 2-keto-3-deoxy-6-phosphogalactonate (KDPGal) was prepared following the method of Toone: Toone, E. J. et al., *J. Mol. Catal. B-Enzymatic*, 1998, 5, 103-11. To a 1 mL quartz cuvette were added 954 μL KH$_2$PO$_4$ buffer (20 mM, pH 7.5), 10 μL NADH (35 mM), 10 μL L-lactic dehydrogenase (L-LDH, EC 1.1.1.27, type II, rabbit muscle, 1 U/μL) and 10 μL appropriately diluted cellular lysate (1:10 to 1:50 dilution in 20 mM KH$_2$PO$_4$, pH 7.5). The solution is mixed and pre-incubated for 2 min at room temperature. The reaction is initiated by addition of KDPGal (16 μL, 100 mg/mL, Li$^+$ salt). The absorbance at 340 nm is recorded continuously for 1 min. One unit of KDPGal aldolase activity is defined by the catalyzed loss of one μmol of NADH per minute.

DAHP Formation Assay

Enzyme activity is measured by following the formation of 3-dehydroshikimic acid (DHS) over time when DHQ synthase (3-dehydroquinate synthase, E.C. 4.2.3.4) and DHQ dehydratase (E.C. 4.2.1.10) are utilized as coupling enzymes. DHQ synthase is prepared as described in Frost, J. W. et al., *Biochemistry*, 1984, 23, 4470-75; DHQ dehydratase is purified from *E. coil* AB2848/pKD201 The reaction (1 mL) contains 50 mM morpholinepropanesulfonic acid (MOPS) buffer (pH 7.5), 1 mM D-erythrose 4-phosphate, 1 mM pyruvate, 50 μM CoCl$_2$, 10 μM NAD, 1 U of DHQ synthase, 1 U of DHQ dehydratase and cellular lysate. The reaction is initiated by addition of diluted cellular lysate to the assay solution, and the absorbance at 234 nm monitored continuously for 5 min. One unit of evolved enzyme activity is defined by the formation of one μmol of DHS per minute.

Error-Prone PCR

Random mutagenesis of dgoA gene is conducted using methods described by Cadwell and Joyce: Cadwell, R. C., Joyce, G. F., PCR *Meth. Appl.*, 1992, 2, 28-33. PCR is performed in a 100 μL reaction mixture containing 10 ng of dgoA fragment as template, 20 mM Tris-HCl, pH 8.4, 50 mM KCl, 7 mM MgCl$_2$, 0.5 mM MnCl$_2$, 0.2 mM dATP, 0.2 mM dGTP, 1.0 mM dCTP, 1.0 mM dTTP, 50 μmol of each primer and 5 U Taq polymerase (Invitrogen). Conditions for PCR are as follows: one cycle of 4 min at 94° C., 22 cycles of 45 sec 94° C., 45 sec 45° C., 45 sec 72° C.; and one cycle of 10 min 25° C.

DNA Shuffling

DNA shuffling is performed following the protocol of Stemmer modified by Zhao and Arnold. See, Stemmer, W. P. C. *Proc. Natl. Acad. Sci. USA* 1994, 91, 10747-10751; Stemmer, W. P. C. *Nature* 1994, 370, 389-391; and Zhao, H.; Arnold, F. H. *Nucleic Acids Res.* 1997, 25, 1307-1308. The 0.6-kb dgoA gene of interest is amplified using Pfu polymerase under standard PCR conditions and cleaned through DNA Clean and Concentrator kit. Fragments for shuffling are created by digesting the cleaned PCR product with DNaseI in a 50 μL reaction containing 5 μg DNA, 50 mM Tris-HCl, pH 8.0, 10 mM MnCl$_2$, and 0.05 U of DNaseI for 10 min at 15° C. The reaction is stopped with addition of 15 μL EDTA (100 mM, pH 8.0) and 12 μL Endostop. Fragments of 20 to 80 bps are purified from 2.0% low melting point agarose gel (Invitrogen) using DE81 ion-exchange paper (Whatman). The purified DNA fragment are dissolved into 30 μL sterile water.

The fragments are reassembled by PCR without primers in a 50 μL reaction containing 20 mM Tris-HCl, pH 8.4, 50 mM KCl, 2 mM MgCl$_2$, 200 μM each dNTPs, 10 μL of DE81 purified DNA fragments and 2.5 U of Taq polymerase. PCR is conducted as follows: 1 min 94° C. followed by 45 cycles of 30 sec 94° C., 30 sec 50° C., 30 sec 72° C., followed by 5 min 72° C. and 5 min 25° C.

The 0.6-kb dgoA genes are reassembled by PCR with forward and reverse primers in a 100 μL reaction containing 5 μL of reassembled DNA, 20 mM Tris-HCl, pH 8.4, 50 mM KCl, 2 mM MgCl$_2$, 200 μM each dNTPs, 50 μmol primers and 5 U of Taq polymerase.

Selection Medium for Directed Evolution of KDPGal Aldolases

Selection medium comprises Na$_2$HPO$_4$ (6 g/L), KH$_2$PO$_4$ (3 g/L), NH$_4$Cl (1 g/L), NaCl (0.5 g/L), glucose (4 g/L), MgSO$_4$ (0.12 g/L), thiamine (6 mg/L), L-leucine (25 mg/L), nicotinic acid (6 mg/L). IPTG is added to a final concentration of 0.2 mM or 0.05 mM. L-Phenylalanine (40 mg/L), L-tyrosine (40 mg/L) and L-tryptophan (40 mg/L) are added as indicated. Solid medium is prepared by addition of 1.5% (w/v) Difco agar to medium solution.

Specific Example 1

Purification of KDPGal Aldolase from *E. coli* and In-Vitro Biosynthesis of 3-Dehydroshikimate

*E. coli* AB3248/pNR5.223 is grown in LB medium containing 50 μg/mL ampicillin at 37° C. IPTG (isopropyl-beta-D-thiogalactopyranoside) is added to a final concentration of 0.2 mM when OD600 reached 0.5. The cells are grown for an additional 6 h, and pelleted by centrifugation (4200 g, 10 min). The cells are washed with 0.9% NaCl solution once and suspended in 20 mM KH$_2$PO$_4$, pH 6.5 with 1 mM PMSF. Disruption of the cells is achieved by two passages through a French pressure cell (16000 psi; 110.3 MPa). Cell debris is removed by centrifugation at 48000 g for 20 min. The resulting crude cell-free lysate is first treated with protamine sulfate and solid (NH$_4$)$_2$SO$_4$, then applied to a DEAE-cellulose (Whatman) column. The column is washed with a gradient mixture of buffer B (20 mM KH$_2$PO$_4$, 50 mM KCl, pH 7.5) and buffer C (20 mM KH$_2$PO$_4$, 400 mM KCl, pH 7.5). Fractions containing KDPGal aldolase are concentrated, dialyzed, quick frozen in liquid nitrogen and stored at −80° C. (87 units/mg).

D-Erythrose 4-phosphate (0.45 mL, 12 mM, pH 7.0), sodium pyruvate (0.054 mL, 100 mM, pH 7.0), CoCl$_2$ (0.027 mL, 10 mM), NAD (0.054 mL, 1 mM), DHQ synthase (2 units) and DHQ dehydratase (2 units) are incubated with KDPGal aldolase (100 units) from *E. coli* at room temperature for 2 h. Protein is subsequently removed by ultrafiltration using Millipore PM-10 membrane. 3-Dehydroshikimate was formed in 90% yield, as determined by $^1$H NMR analysis.

Specific Example 2

Cloning and Characterization of dgoA Genes from Other Bacterial Sources.

*E. coli* wild-type dgoA-encoded KDPGal aldolase showed weak activity toward accepting D-erythrose 4-phosphate as a substrate. KDPGal aldolases from other bacterial sources might have higher activities for catalyzing the condensation of pyruvate with D-erythrose 4-phosphate. Obtaining dgoA genes from other bacteria would also enable a cross-species DNA family shuffling that has been reported to improve enzyme performance rapidly. Although KDPGal aldolase activities have been identified in *Pseudomonas saccarophila, Pseudomonas cepacia, Caulobacter cresentus, Azotobacter vinelandii, Rhizobium meliloti, Gluconobacter liquefaciens,* and nonpathogenic *Mycobacteria*, none of these dgoA gene sequences was known except in *Caulobacter cresentus* in which the genomic sequence has been obtained. See: Crameri, A. et al., *Nature* 1998, 391, 288-291; Kurn, N. et al., *J. Bacteriol.* 1978, 135, 517-520; Wong, T. Y.; Yao, X., *Appl. Environ. Microbiol.* 1994, 60, 2065-2068; Arias, A.; Cervenansky, C., *J. Bacteriol.* 1986, 167, 1092-1094; Stouthammer, A. H., *Biochim. Biophys. Acta* 1961, 48, 484-500; Szumilo, T., *Mycobacteria*. J. Bacteriol. 1981, 148, 368-370; and Nierman, W. C. et al., *Proc. Natl. Acad. Sci. USA* 2001, 98, 4136-4141.

Performing a BLAST (Basic Local Alignment Search Tool) search against *E. coli* dgoA nucleotides sequence in microbial genome database only yielded two possible dgoA sequences from *Klebsiella pneumoniae* and *Salmonella typhimurium* LT2. BLAST search against the *E. coli* dgoA protein sequence afforded several more hits including Caulobacter cresentus CB15, *Agrobacterium tumefaciens, Ralstonia solanacearum, Bradyrhizobium japonicum, Brucella melitensis* and *Sinorhizobium meliloti*. The genomic DNA of *K. pneumoniae, S. typhimurium* LT2 (ATCC 15277), *A. tumefaciens* (ATCC 17805) and *C. cresentus* CB15 (ATCC 19089) are readily available from the American Type Culture Collection (ATCC). Thus, the open reading frames of the *K. pneumoniae, S. typhimurium* LT2, *A. tumefaciens* and *C. cresentus* CB15 dgoA genes were amplified from their respective genomic DNA using PCR and cloned into a medium copy number expression vector pJF118EH with transcription under the control of a $P_{tac}$ promoter to prepare plasmid pNR6.252, pNR7.120, pNR6.300 and pNR7.063, respectively. The native start codon of GTG in *C. cresentus* dgoA was changed into an ATG start codon in plasmid pNR7.063. The corresponding plasmids were transformed into *E. coli* CB734, and in all cases, the KDPGal aldolase activities in crude cell lysates were confirmed and determined (Table 1).

TABLE 1

KDPGal Aldolases from Various Microorganisms.

| dgoA source | dgoA size (nt) | Identity[a] with E. coli dgoA | KDPGal cleavage[b] | DAHP formation[b] |
|---|---|---|---|---|
| *Escherichia coli*[c] | 618 | 100% | 7.6 | 0.068 |
| *Klebsiella pneumoniae*[d] | 618 | 82% | 77 | 0.29 |
| *Salmonella typhimurium*[e] | 618 | 81% | 10 | 0.080 |
| *Agrobacterium tumefaciens*[f] | 630 | 54% | 4.8 | 0.30 |
| *Caulobacter cresentus*[g] | 582 | 60% | 3.6 | 0.23 |

[a]Identity is calculated based on nucleotide sequence using the global sequence alignment provided by Biology Workbench (http://workbench.sdsc.edu); see Pearson, W. R.; Lipman, D. J., Improved tools for biological sequence comparison, Proc. Natl. Acad. Sci. USA 1988, 85, 2444-2448, and Pearson, W. R., Rapid and sensitive sequence comparison with FASTP and FASTA, Methods Enzymol. 1990, 83, 63-98.
[b]Specific activity is defined as units of enzyme activity per mg of protein in crude cell lysate. One unit of activity = one μmol of KDPGal cleaved or DAHP formed per minute.
[c]*E. coli* CB734/pNR7.088.
[d]*E. coli* CB734/pNR6.252.
[e]*E. coli* CB734/pNR7.120.
[f]*E. coli* CB734/pNR6.300.
[g]*E. coli* CB734/pNR7.063.

All of the bacteria identified in the BLAST searches are members of the proteobacteria. Thus, in a preferred embodiment of a recombinant KDPGal aldolase according to the present invention, the amino acid sequence of the recombinant will be a variant of the amino acid sequence of a native (i.e. wild-type) KDPGal aldolase obtained from a member of the bacteria; in a preferred embodiment, it will be obtained from a member of the proteobacteria. In methods and pathways according to the present invention, the KDPGal aldolase(s) used therein may have either a native or a mutant KDPGal aldolase amino acid sequence. Where a native KDPGal aldolase amino acid sequence is utilized, in a preferred embodiment, it will be obtained from a member of the bacteria; in a preferred embodiment, it will be obtained from a member of the proteobacteria. In a preferred embodiment, a bacterium providing such a native amino acid sequence will be a member of any one of the genera *Escherichia, Klebsiella, Salmonella, Caulobacter, Agrobacterium, Ralstonia, Bradyrhizobium, Brucella,* and *Sinorhizobium.*

The KDPGal aldolases of *E. coli* (SEQ ID NO:2), *K. pneumoniae* (SEQ ID NO:4), and *S. typhimurium* (SEQ ID NO:6), were all found to be 205 residues in length. The remaining KDPGal aldolases identified from BLAST analyses of genomic DNA, were found to range from 194 to 213 residues in length. In a preferred embodiment, a KDPGal aldolase according to the present invention will be about 190 to about 215 residues; in a preferred embodiment, it will be about 200 to about 210 residues; and in a preferred embodiment, it will be about 205 residues in length.

Among the five KDPGal aldolases, *K. pneumoniae* and *A. tumefaciens* KDPGal aldolases showed highest activities toward DAHP formation (see Table 1). The dgoA gene coding sequences of *K. pneumoniae* (SEQ ID NO:3) and *S. typhimurium* LT2 (SEQ ID NO:5) were found to have the highest nucleotide sequence homology of about 81% with that of the *E. coli* dgoA (SEQ ID NO:1) (see Table 1).

Specific Example 3

Directed Evolution of KDPGal Aldolases

The dgoA genes of *E. coli, K. pneumoniae,* and *S. typhimurium* were each evolved by use of error-prone PCR and DNA shuffling. *E. coli* dgoA and *K. pneumoniae* dgoA and were subjected to two rounds of error-prone PCR mutagenesis followed by one round of DNA shuffling. Identification of increased activity relative to condensation of pyruvate with D-erythrose 4-phosphate was based on a selection that increased in stringency with each round of directed evolution.

The activity of the resulting KDPGal aldolases in catalyzing condensation of pyruvate and D-erythrose 4-phosphate was investigated in *E. coli* CB734, which lacks all isozymes of DAHP synthase. Thus, growth of *E. coli* CB734 on glucose-containing minimal salts medium required supplementation with L-phenylalanine, L-tyrosine, L-tryptophan and aromatic vitamins (entry 1, Tables 2-4, below).

TABLE 2

Directed Evolution of *E. coli* KDPGal aldolase.

| Entry | Construct[a] | M9[b] | M9[c] | F[d] | YF[d] | YFW[d] | YFWvit[d] |
|---|---|---|---|---|---|---|---|
| 1 | *E. coli* CB734 | −[e] | − | − | − | − | +[f] |
| 2 | CB734/pNR7.088 | − | − | − | − | + | + |
| 3 | CB734/pEC01 | − | − | − | + | + | + |
| 4 | CB734/pEC02 | − | + | + | + | + | + |
| 5 | CB734/pEC03 | + | + | + | + | + | + |

[a]All native and evolved dgoA genes were inserted into the same plasmid (pTrc99A) with transcription controlled by a Ptrc promoter.
[b]Contained L-leucine and 0.05 mM IPTG.
[c]Contained L-leucine and 0.2 mM IPTG.
[d]Supplements added to M9 medium containing L-leucine and 0.2 mM IPTG included: F, L-phenylalanine; Y, L-tyrosine; W, L-tryptophan; vit, p-aminobenzoate, p-hydroxybenzoate, 2,3-dihydroxybenzoate.
[e]no growth (−).
[f]growth (+).

TABLE 3

Directed Evolution of *K. pneumoniae* KDPGal Aldolase

| Entry | Construct[e] | M9[a] | M9[b] | F[c] | YF[c] | YFW[c] | YFWvit[c] |
|---|---|---|---|---|---|---|---|
| 1 | *E. coli* CB734 | −[d] | − | − | − | − | +[e] |
| 2 | CB734/pNR7.118 | − | − | − | − | + | + |
| 3 | CB734/pNR6.252 | − | − | − | + | + | + |
| 4 | CB734/pKP01 | − | − | + | + | + | + |
| 5 | CB734/pKP02 | − | + | + | + | + | + |
| 6 | CB734/pKP03 | + | + | + | + | + | + |

[a]contained 0.05 mM IPTG.
[b]contained 0.2 mM IPTG.
[c]Supplements added to M9 medium containing 0.2 mM IPTG included: F, L-phenylalanine; Y, L-tyrosine; W, L-tryptophan; vit, p-aminobenzoate, p-hydroxybenzoate, 2,3-dihydroxybenzoate.
[d]growth (+).
[e]no growth (−).
[e]All native and evolved dgoA genes were inserted into the same plasmid (pJF118EH) with transcription controlled by a Ptac promoter.

TABLE 4

Directed Evolution of *S. typhimurium* KDPGal Aldolase

| Entry | Construct[a] | M9[b] | M9[c] | F[d] | YF[d] | YFW[d] | YFWvit[d] |
|---|---|---|---|---|---|---|---|
| 1 | *E. coli* CB734 | −[e] | − | − | − | − | +[f] |
| 2 | CB734/pNR7.120 | − | − | − | − | + | + |
| 3 | CB734/pST01 | − | − | − | + | + | + |
| 4 | CB734/pST02 | − | − | + | + | + | + |
| 5 | CB734/pST03 | − | + | + | + | + | + |
| 6 | CB734/pST04 | + | + | + | + | + | + |

[a]All native and evolved dgoA genes were inserted into the same plasmid (pJF118EH) with transcription controlled by a $P_{tac}$ promoter.
[b]Contained L-leucine and 0.05 mM IPTG.
[c]Contained L-leucine and 0.2 mM IPTG.
[d]Supplements added to M9 medium containing L-leucine and 0.2 mM IPTG included: F, L-phenylalanine; Y, L-tyrosine; W, L-tryptophan; vit, p-aminobenzoate, p-hydroxybenzoate, 2,3-dihydroxybenzoate.
[e]no growth (−).
[f]growth (+).

It was also found that *E. coli* CB734/pNR7.118 with its mid-encoded *E. coli* DgoA was able to biosynthesize its own aromatic ins (entry 2, Table 3). Plasmid-encoded *K. pneumoniae* DgoA afforded old higher KDPGal aldolase specific activity in *E. coli* CB734/pNR6.252 relative to plasmid-encoded *E. coli* DgoA in *E. coli* CB734/pN7.118. *E. coli* CB734/pNR6.252 was able to provide for its own aromatic vitamin and L-tryptophan requirements (entry 3, Table 3).

A. Evolution of KDPGal Aldolase from *E. coli*

The dgoA gene encoding the native *E. coli* KDPGal aldolase is amplified under mutagenic (error-prone) PCR condition with the following primers, JWF 484 5'-GACGGATC-CTATAAGGAGCATCGCTCATG (SEQ ID NO:33), JWF 529 3'-GAAGCTGCAGTCATTGCACTGCCTCTCGAT (SEQ ID NO:34). The 0.6-kb *E. coli* dgoA amplification product is purified, digested with restriction enzymes BamHI and PstI. The fragments are cloned into the corresponding sites of pTrc99A and transformed into competent CB734 cells by electroporation to generate the first generation plasmid library. After transformation, a library of 1×10⁶ colonies are spread on minimal salts plates supplement with tyrosine and phenylalanine with 0.2 mM IPTG. After incubation at 37° C. for 3 days, 50 large colonies were picked up and a plasmid mixture (pEC01-mix) are prepared. For the second round of selection, the mutant 0.6-kb dgoA gene is isolated and further amplified under mutagenic PCR condition, the fragments are cloned into pTrc99A vector. A library of 1×10⁶ colonies is spread on minimal salts plates with 0.2 mM IPTG without any aromatic amino acids supplementation. More than 100 colonies are produced after 4 days of incubation, 50 large colonies replicated on a LB/Ap plate. After overnight incubation, the cells are scraped from the plate with sterile water and a plasmids mixture was prepared (pEC02-mix). For the third round, the 0.6-kb fragments encoding the mutant DgoA are PCR amplified from the pEC0$_2$-mix, the fragments aer shuffled to combine the beneficial point mutations and cloned into pTrc99A as above. A library of 3×10$^5$ colonies are spread on minimal salts plates with 0.05 mM IPTG. After 3 days at 37° C., 7 largest colonies are picked up for characterization. See Table 5, below.

TABLE 5

Mutations and Specific Activities of *E. coli* KDPGal Aldolase Variants

| DgoA | Mutations | DAHP formation sp. activity$^a$ (U/mg) |
|---|---|---|
| Wild-type |  | 0.086 |
| EC03-1 | F33I, D58N, Q72H, A75V, V85A, V154F | 0.56 |
| EC03-2 | D30G, F33I, D34G, S42T, A75T, V85A, V154F, L179I, A182P | 0.30 |
| EC03-3 | F33I, D34G, K59R, V85A, A111P, G134S, P135L, V154F, P159A | 0.56 |
| EC03-4 | F33I, D34G, S42T, D74N, V85A, A122V, V154F, D167E, A190T | 0.32 |
| EC03-5 | S42T, K59M, V85A, A122V, V154F, D178V | 0.37 |
| EC03-6 | S42T, V85A, H90Y, V154F, L175I | 0.32 |
| EC03-7 | K6N, T17M, V85A, I89T, V154F, S185P | 0.29 |

$^a$*E. coli* CB734 was used as host strain for expression of the evolved enzymes.

B. Evolution of KDPGal Aldolase from *K. pneumoniae*

*K. pneumoniae* dgoA is amplified under mutagenic PCR conditions with the following primers, JWF559 5'-GGMT-TCGACAGGMTAAGGAGCATCG (SEQ ID NO:31) and JWF560 5'-GACGGATCCTCATTTCACTGCCTCTCGAT (SEQ ID NO:32). The 0.6-kb amplification product is purified through DNA Clean and Concentrator kit, followed by double digestion with restriction enzymes EcoRI and BamHI, and cloned into the EcoRI-BamHI restriction site of expression vector pJF118EH to generate the first generation plasmid library. The plasmid library is electroporated into CB734 and a library of 1×10$^6$ colonies are plated out on minimal salts plates with phenylalanine and 0.2 mM IPTG supplementation. L-Leucine is added throughout the selection since CB734 is also a leucine-auxotrophy strain. A single colony is produced after 48 h incubation at 37° C., and the plasmid carrying the first generation mutant KP01-1 prepared from the colony. For the second generation, KP01-1 is amplified under mutagenic PCR conditions and cloned as above. A library of 6×10$^5$ colonies are spread on minimal salts plates with 0.2 mM IPTG and no aromatic amino acids supplementation. After 4 days incubation at 37° C., 50 largest colonies were picked up and a mixture of the plasmid was prepared. For the third round, the mutated dgoA genes KP02 were fragmented and shuffled to combine beneficial point mutations and subsequent cloned and transformed as before. A library of 3×10$^4$ colonies are spread on minimal salts plates with 0.05 mM IPTG. After 3 days at 37° C., 7 largest colonies were picked up for characterization. See Table 6 below.

TABLE 6

Mutations and Specific Activities of *K. pneumoniae* KDPGal Aldolase Variants

| DgoA | Mutations | DAHP formation sp. activity$^a$ (U/mg) |
|---|---|---|
| Wild-type |  | 0.29 |
| KP03-1 | I10V, V85A, V154F, E187D, F196I | 0.80 |
| KP03-2 | I10V, P70L, V85A, P106S, V154F, S185L, F196I | 0.15 |
| KP03-3 | I10V, E71G, V85A, P106S, V154F, E187D, Q191H, F196I | 1.30 |
| KP03-4 | I10V, V85A, V154F, A195T, F196I | 0.51 |
| KP03-5 | I10V, I16V, P70L, V85A, R96Q, P106S, V154F, F196I | 0.049 |
| KP03-6 | I10V, V85A, V154F, F196I | 0.66 |
| KP03-7 | I10V, V85A, P106S, V154F, F196I | 0.65 |

$^a$*E. coli* CB734 was used as host strain for expression of the evolved enzymes.

C. Evolution of KDPGal Aldolase from *S. typhimurium*.

*S. typhimurium* dgoA was subjected two rounds of error-prone PCR mutagenesis and two rounds of DNA shuffling. The plasmid library from the first round of error-prone PCR mutagenesis was electroporated into *E. coli* CB734 and plated out onto minimal salts plates containing L-tyrosine, L-phenylalanine and 0.2 mM IPTG. *E. coli* CB734/pST01 (entry 3, Table 4) colonies resulted from the first round of PCR mutagenesis performed using wild-type *S. typhimurium* dgoA as template only required L-tyrosine and L-phenylalanine supplementation for growth. The second round of PCR mutagenesis gave *E. coli* CB734/pST02 colonies (entry 4, Table 4) whose growth required only L-phenylalanine supplementation. The third round of mutagenesis involving shuffling gave *E. coli* CB734/pST03 colonies that grew in the absence of aromatic amino acids supplements (entry 5, Table 4). The fourth round of mutagenesis involving shuffling gave CB734/pST04 colonies that grew in minimal salts medium without aromatic amino acids supplementation at reduced KDPGal aldolase expression level by lowering IPTG concentration (entry 6, Table 4). The dgoA gene variants from seven largest colonies after the final round of selection were sequenced and their encoding KDPGal aldolase activities toward DAHP formation were characterized (Table 7). All seven evolved KDPGal aldolase showed higher activity toward DAHP formation activity as compared to the wild-type *S. typhimurium* KDPGal aldolase. The most active mutant ST04-5 showed a 15-fold increase in activity.

TABLE 7

Mutations and Specific Activities of *S. typhimuriume* KDPGal Aldolase Variants.

| DgoA | Mutations | DAHP activity$^a$ (U$^b$/mg) |
|---|---|---|
| Wild-type |  | 0.080 |
| ST04-1 | V28L, S42T, S50P, P150L, L175S | 0.48 |
| ST04-2 | V28M, S42T, S50P, P150L, D178G, N198K | 0.85 |
| ST04-3 | D20E, V28L, S42T, L175S | 0.84 |
| ST04-4 | V28M, S42T, Q123R, T158M, N161D, D178G | 0.54 |
| ST04-5 | D20E, V28M, S42T, I89T, P150L, D178G | 1.24 |
| ST04-6 | V28M, S42T, S50P, Q164A, L175S, N198K | 0.42 |
| ST04-7 | V28L, S42T, P91Q, P150L, T158M, D178G, N198K | 1.04 |

$^a$*E. coli* CB734 was used as host strain for expression of evolved enzymes.
$^b$One unit of DAHP synthase catalyzes the formation of one μmol of 3-dehydroshikimate per minute at 25° C.

D. Characterization of E. coli, K. pneumoniae and S. typhimurium DgoA Mutants

After directed evolution, a total of twenty-one active mutants selected from the E. coli, K. pneumoniae and S. typhimurium DgoA mutants were further characterized. Each mutant contained 4-9 amino acids substitutions. No insertion or deletion mutants were found. Two amino acids substitutions (V85A, V154F) were observed in all of the seven most active K. pneumoniae DgoA and seven most active E. coli dgoA mutants. However, these two mutations were not found in any of the seven most active S. typhimurium mutants. Instead, all seven of the most active S. typhimurium mutants contained a S42T substitution, as did four of the seven most active E. coli mutants. EC03-1, the most active evolved E. coli KDPGal aldolase, exhibited an 8-fold higher DAHP formation specific activity and a 7-fold reduced KDPGal cleavage specific activity relative to the native E. coli KDPGal aldolase (entry 2, Table 8). KP03-3, the most active evolved K. pneumoniae KDPGal aldolase, showed a 4-fold higher DAHP formation specific activity and a 30-fold reduced KDPGal cleavage specific activity relative to native K. pneumoniae KDPGal aldolase (entry 4, Table 8). ST04-5, the most active evolved S. typhimurium KDPGal aldolase, exhibited a 15-fold higher DAHP formation specific activity and a 2-fold reduced KDPGal cleavage specific activity relative to wild-type S. typhimurium KDPGal aldolase (entry 6, Table 8).

TABLE 8

Specific Activities of Wild-Type and Evolved KDPGal Aldolase Isozymes.

| Enzyme | DAHP assay$^a$ (U/mg) | KDPGal assay$^a$ (U/mg) |
|---|---|---|
| E. coli DgoA$^b$ | 0.068 | 6.7 |
| EC03-1$^c$ | 0.56 | 1.0 |
| K. pneumoniae DgoA$^d$ | 0.29 | 77 |
| KP03-3$^e$ | 1.30 | 2.6 |
| S. typhimurium DgoA$^f$ | 0.080 | 11 |
| ST04-5$^g$ | 1.24 | 4.8 |

$^a$Specific activity is defined as units of enzyme activity per mg of protein in crude cell lysates. One unit of activity = one μmol of KDPGal cleaved or DAHP formed per minute. Crude cell lysates were prepared from
$^b$E. coli CB734/pNR7.088;
$^c$E. coli CB734/pEC03-1;
$^d$E. coli CB734/pNR6.252;
$^e$E. coli CB734/pKP03-3;
$^f$E. coli CB734/pNR7.120;
$^g$E. coli CB734/pST04-5.

In addition to V85A and Vi 54F, two other amino acid substitutions (I10V, F196I) were found in all seven of the most active K. pneumoniae mutants. Only one substitution was found in all seven of the most active S. typhimurium mutants; however, a conservative substitution at V28 (either V28M or V28L) was also found in all seven mutants. One amino acid substitution (P70L) was observed solely in the two active K. pneumoniae mutants identified as exhibiting less activity than wild-type K. pneumoniae DgoA; however, these two mutants still exhibited significant aldolase activity, with one of them (KP03-2) exhibiting greater DAHP formation activity than either of the E. coli or S. typhimurium wild type enzymes.

In sum, the following amino acid mutations were identified as being associated with improved mutants of the E. coli, K. pneumoniae, and S. typhimurium DgoA enzymes: X10V, X28L or X28M, X42T, X85A, X154F, and X196I ("X" representing any amino acid residue at that position), more specifically, I10V, V28L or V28M, S42T, V85A, V154F, and F196I. Thus, in a preferred embodiment of a recombinant KDPGal aldolase according to the present invention, the KDPGal aldolase will contain at least one of said mutations. Likewise, the following amino acid mutation was identified as being associated with impaired, though active, mutants of the K. pneumoniae enzyme: X70L, more specifically, P70L. Thus, in a preferred embodiment of a recombinant KDPGal aldolase according to the present invention, the KDPGal aldolase will contain no mutation that is X70L.

The mutations were characterized at the DNA level as follows, with nucleotide substitutions and codon substitutions shown in parentheses:

I10V (a28g; atc28-30gtc); V28M (g82a; gtg82-84atg); V28L (g82t; gtg82-84ttg); S42T (t124a; tcc124-126acc); V85A (t254c; gtt253-255gct); V154F (g460t; gtt460-462ttt); and F196I (t586a; ttc586-588atc).

Specific Example 5

DgoA Family Shuffling

Family shuffling of all five dgoA genes constitutes one option for improving DAHP formation activity. However, a major limitation cited for family shuffling of homologous genes is its reliance on PCR-based assembly of short random fragments generated from homologous genes. This demands a level of sequence identity of more than 70% and 10-15 bp stretches of continuous sequence identity between sequences in order for recombination to occur. Therefore, only K. pneumoniae and S. typhimurium LT2 KDPGal aldolase were subjected to directed evolution by PCR mutagenesis and DNA shuffling, followed by DNA family shuffling of the most evolved K. pneumoniae (KP03-3) and S. typhimurium (ST04-5) KDPGal aldolase mutants with the most evolved E. coli KDPGal aldolase mutant (EC03-1).

The dgoA mutants, EC03-1, KP03-3 and ST04-5, were subjected to DNA family shuffling using the single-stranded DNA shuffling method developed by Zhao and coworkers: Zha, W; Zhu, T; Zhao, H., Methods Mol. Biol. 2003, 231, 91-97. Sequencing a small library of mutants (76) obtained from the family shuffling revealed a crossover rate of approximately 1.4 per gene using the published protocol. E. coli CB734 was transformed with a plasmid library that contained the chimeric dgoA hybrids (NR8.165), and the colonies that showed higher growth rate in the absence of aromatic amino acids supplementation as compared to E. coli CB734 carrying plasmid containing the parent gene, EC03-1, KP03-3 or ST04-5 (colonies appeared after 3 days on minimal salts medium) were selected. The dgoA gene hybrids from the five largest colonies that appeared after 2.5 days were sequenced and their encoding KDPGal aldolase activities toward DAHP formation were determined as shown in Table 9.

TABLE 9

Chimeric dgoA Genes Evolved by Cross-Species DNA Family Shuffling.

| entry | family shuffling mutants | dgoA structure$^a$ | DAHP formation$^b$ (U$^c$/mg) |
|---|---|---|---|
| 1 | NR8.165-2 | | 1.31 |
| 2 | NR8.165-3 | | 0.30 |
| 3 | NR8.165-4 | | 0.22 |
| 4 | NR8.165-5 | | 0.10 |
| 5 | NR8.165-6 | | 0.56 |

$^a$Symbol: EC03-1; KP03-3; ST04-5.
$^b$Each dgoA mutant was inserted into the same plasmid (pJF118EH) with transcription controlled by a P$_{tac}$ promoter. E. coli CB734 was used as host strain for expression of evolved enzymes.
$^c$One unit of DAHP synthase catalyzes the formation of one μmol of 3-dehydroshikimate per minute at 25° C.

All five mutants were found to be chimeras of genes from the E. coli, K. pneumoniae and S. typhimurium. Four of them contain two segments resulting from a single crossover event. One mutant, NR8.165-4, contains three segments resulting from two crossovers. It also noteworthy that most crossover events occurred in the first 40-80 base pairs area where the three genes have 40-base pairs of nearly identical sequences. Compared with the wild-type E. coli KDPGal aldolase, the DgoA mutant NR8.165-4 has a 5-fold increase in $k_{cat}$ and a 5-fold reduction in $K_m$ for D-erythrose 4-phosphate, and thus a 25-fold increase in $k_{cat}/K_m$ (entry 7, Table 10). Both the mutant NR8.165-2 and NR8.165-6 show a decrease in $k_{cat}/K_m$ values relative to their parent enzymes (entries 6 and 8 vs. entries 4 and 5, Table 9). The $K_m$ value ranging from 80 to 157 µM for D-erythrose 4-phosphate of the mutant enzymes is close to the $K_m$ value of E. coli native DAHP synthase for D-erythrose 4-phosphate: AroF: $K_m$=81.4 µM, $k_{cat}$=29.5 s$^{-1}$; AroG: $K_m$=141 µM, $k_{cat}$=10.3 s$^{-1}$; AroH: $K_m$=35 µM, $R_{cat}$=20.6 s$^{-1}$. References are: Ramilo, C. A.; Evans, J. N. S., Protein Express. Purif. 1997, 9, 253-261 (for AroF); Sheflyan, G. Y. et al., J. Am. Chem. Soc. 1998, 120, 11027-11032 (for AroG); and Akowski, J. P.; Bauerle, R., Biochemistry 1997, 36, 15817-15822 (for AroH). However, the $k_{cat}$ of the mutant DgoAs is significantly lower than the $k_{cat}$ of the native DAHP synthases.

TABLE 10

Kinetic Parameters of the Wild-Type KDPGal Aldolases and the Evolved Variants from Cross-Species DNA Family Shuffling.

| Entry | DgoA[a] | $K_m$ (E4P, µM) | $k_{cat}$ (s$^{-1}$) | $k_{cat}/K_m$ (µM$^{-1}$ s$^{-1}$) |
|---|---|---|---|---|
| 1 | Wild-type E. coli | 571 | 0.94 | 1.65 × 10$^{-3}$ |
| 2 | wild-type K. pneumoniae | 1507 | 1.39 | 3.22 × 10$^{-4}$ |
| 3 | wild-type S. typhimurium | 685 | 0.600 | 3.76 × 10$^{-3}$ |
| 4 | EC03-1 | 124 | 2.49 | 2.01 × 10$^{-2}$ |
| 5 | ST04-5 | 119 | 3.24 | 2.72 × 10$^{-2}$ |
| 6 | NR8.165-2 | 157 | 2.51 | 1.60 × 10$^{-2}$ |
| 7 | NR8.165-4 | 115 | 4.76 | 4.14 × 10$^{-2}$ |
| 8 | NR8.165-6 | 80 | 0.504 | 6.30 × 10$^{-3}$ |

[a]All wild-type and the evolved KDPGal aldolases were expressed and purified as GST (glutathione S-transferase) fusion proteins.

Specific Example 5

Characterization of Pyruvate-Based Shikimate Synthesis Pathway In Vivo

To examine the functioning of created shikimate pathway variant in intact microbes, growth rates and synthesis of 3-dehydroshikimate were examined. E. coli CB734/pEC03-1 and E. coli CB734/pKP03-3 were completely dependent on plasmid-encoded, evolved DgoA isozymes EC03-1 and KPO3-3, respectively, for the formation of DAHP. E. coli CB734/pNR7.126 relied on plasmid-encoded, feedback-insensitive AroF$^{FBR}$ for DAHP synthase activity. When cultured under identical conditions where growth was dependent on de novo synthesis of aromatic amino acids and aromatic vitamins, E. coli CB734/pEC03-1 and E. Coli CB734/pKP03-3 entered the logarithmic phases of their growths 36 h and 12 h, respectively, later than E. coli CB734/pNR7.126 This is depicted in FIG. 4, showing growth in the absence of aromatic amino acid and aromatic vitamin supplements in glucose-containing minimal salts medium under shake-flask conditions: E. coli CB734/pNR7.126 (squares); E. coli CB734/pEC03-1 (circles); E. coli CB734/pKP03-3 (triangles).

Synthesis of 3-dehydroshikimate employed E. coli NR7, which was constructed from E. coli KL3 using site-specific chromosomal insertions to inactivate all DAHP synthase isozymes. E. coli KL3 has been extensively used in studies examining the impact of phosphoenolpyruvate availability on the synthesis of 3-dehydroshikimate. Constructs were cultured under identical fermentor-controlled conditions. E. coli NR7/pKP03-3serA synthesized 8.3 g/L of 3-dehydroshikimate in 48 h in 5% yield from glucose. Only a trace amount of this product was synthesized by NR7/pNR8.074, which expressed plasmid-encoded, native K. pneumoniae DgoA. E. coli NR7/pEC03-1serA synthesized 12 g/L of 3-dehydroshikimate in 5% yield from glucose. For comparison, 2.0 g/L of 3-dehydroshikimate was synthesized in 0.9% yield by E. coli NR7/pNR8.075, which expressed plasmid-encoded, native E coli DgoA.

Further characterization of the pyruvate-based shikimate pathways according to the present invention was performed in fed-batch fermentations (36° C., pH 7.0, 20% air saturation, with growth on glucose-containing medium). In some cases, the host cell was further transformed with a polynucleotide encoding a transketolase (E.C. 2.2.1.1), a key enzyme responsible for the in vivo synthesis of E4P, whose low concentration can present a bottleneck in the DAHP synthesis process; overexpression thereof can enhance the yield of DAHP, and thus of DHQ, DHS, and further DHS derivates, e.g., shikimate. An E. coli tktA gene provided the coding sequence used therein (SEQ ID NO:9), although various transketolase isozymes may be used to supplement in vivo production of E4P, e.g., tktB gene-encoded enzymes, such as the E. coli TktB (SEQ ID NO:12). Alternatively, a transaldolase (E.C. 2.2.1.2) may be employed for this purpose. Exemplary transaldolases include, e.g., E. coli isozymes TalA (e.g., GenBank Accession No. D13159; gi:2337773) and TalB (e.g., GenBank Accession No. D13161; gi:2337775).

E. coli CB734 was not used for fed-batch fermentation of 3-dehydroshikimic acid in this study due to its L-leucine requirement and difficulty in comparing product titer and yield with previously reported 3-dehydroshikimic acid synthesis by constructs based on E. coli KL3. Therefore, instead of constructing a CB734aroEydiB$^-$ strain, E. coli NR7 was constructed. All three DAHP synthase genes (aroF, aroG, aroH) in E. coli NR7 were inactivated by site-specific chromosomal insertions carried out in E. coli strain KL3 (AB2834 serA::aroB).

The DAHP synthase encoded by aroF and aroH in E. coli CB734 were inactivated by insertion with a chloramphenicol-resistant (Cm$^R$) gene and a kanamycin-resistance gene (Kan$^R$), respectively. P1-phage mediated transformation from E. coli CB734 could be the simplest way to disrupt the corresponding aroF and aroH genes in E. coli KL3 directly. Unfortunately, E. coli CB734 was found to be a P1 phage resistant strain possibly due to deletion of the gal operon in its chromosome. Transforming a plasmid-localized galE encoding UDP-galactose-4-epimerase in E. coli CB734 failed to reverse the P1 phage resistance phenotype of E. coli CB734.

Chromosomal inactivation of DAHP synthase genes aroF, aroG, aroH were then carried out by homologous recombination methods. Special recombinant-proficient E. coli hosts lacking exonuclease V of the RecBCD recombination complex are suitable for chromosomal recombination by transforming with linear DNA. Recombination can occur in recB or recC mutants carrying a suppressor sbcB mutation that enhances recombination by the RecF pathway or in recD mutants that are recombinase proficient but lack exonuclease V. A simple one-step method applicable to wild-type E. coli strain has been developed to use the bacteriophage A Red recombinase to mediate recombination using linear DNA with short homolog extensions.

To construct *E. coli* NR7, the chloramphenicol-resistant (CM$^R$) gene was inserted into aroF in a plasmid. The aroF::Cm$^R$ allele was isolated and transformed into strain JC7623, a hyper-recombinant recBC sbcBC strain. Chloramphenicol-resistant transformants JC7623aroF::Cm$^R$ in which the wild-type aroF was exchanged with aroF::Cm$^R$ allele by double-crossover event were obtained on chloramphenicol plates. P1-phage mediated transduction of JC7623aroF::Cm$^R$ transferred the aroF::Cm$^R$ mutation into KL3 to generate *E. coli* KL3aroF::Cm$^R$. Similarly, the aroH::Kan$^R$ mutation was transferred from JC7623aroH::Kan$^R$ to KL3aroF::Cm$^R$ to prepare *E coli* KL3aroF::Cm$^R$ aroH::Kan$^R$. However, attempted transfer of the aroG::tet mutation by P1 phage mediated transduction from JC7623aroG::Tc$^R$ was not successful. The aroG mutation was then generated using the λ Red recombinase method. An aroG::Tc$^R$ DNA fragment was electroporated into KL3aroF::Cm$^R$ aroH::Kan$^R$ carrying a plasmid pKD46 encoding λ Red recombinase. Recombinants were selected for tetracycline resistance (5 μg/mL) at 30° C. Plasmid pKD46 was eliminated by growth at 42° C. Disruption of chromosomal aroG was confirmed by PCR from NR7 genomic DNA using a pair of primers flanked the aroG locus to amplify a fragment corresponding to the aroG::tet allele with correct size. The *E. coli* KL3aroF::Cm$^R$ aroG::Tc$^R$ aroH::Kan$^R$ strain was designated as *E coli* NR7.

In directed evolution of *E. coli* KDPGal aldolase, *E. coli* dgoA mutants were expressed under the control of a $P_{trc}$ promoter in expression vector pTrc99A, while *K. pneumoniae* and *S. typhimurium* dgoA mutants were expressed under a tac promoter in pJF118EH. The trc promoter displays a spacing of 17 bp between the −35 and −10 consensus sequences$^a$ compared to a spacing of 16 bp between these regions in the tac promoter. Despite the 1 bp difference in spacing, $P_{tac}$ and $P_{trc}$ promoters are virtually of identical strength. However, plasmid pTrc99A does have a smaller size (4.2-kb vs. 5.3-kb in pJF118EH) and an increased plasmid copy number per chromosome (30 vs. 18 in pJF118EH) compared to plasmid pJF118EH. Therefore, the most active evolved *E. coli* mutant EC03-1 was excised from pEC03-1 and cloned into the pJF118EH vector to afford plasmid pNR8.140. Plasmid pNR8.158, pKP03-3serA and pST04-5serA were constructed by inserting a serA gene into the plasmids containing the corresponding dgoA mutants. Including the serA locus on plasmid provides the basis for plasmid maintenance during cultivation in minimal salts medium lacking L-serine supplementation. Furthermore, expression of the dgoA mutants in the same plasmid enabled an unbiased comparison of the in vivo activities of the individually evolved KDPGal aldolases in terms of the production of the pyruvate-based shikimate pathway metabolite.

TABLE 11

Synthesis of 3-dehydroshikimic acid under fermentor-controlled conditions.

| Entry | Construct | Genes | DHS$^a$ (g/L) | DHS (yield$^b$) |
|---|---|---|---|---|
| 1 | NR7/pKP03-3serA | $P_{tac}$KP03-3, serA | 8.3 | 5.0% |
| 2 | NR7/pNR8.074 | $P_{tac}$wt-KPdgoA, serA | 0 | 0 |
| 3 | NR7/pNR8.172 | $P_{tac}$EC03-1, serA | 5.1 | 2.4% |
| 4 | NR7/pNR8.170 | $P_{tac}$wt-ECdgoA, serA | 0 | 0 |
| 5 | NR7/pST04-5serA | $P_{tac}$ST04-5, serA | 6.9 | 3.3% |
| 6 | NR7/pNR8.121 | $P_{tac}$wt-STdgoA, serA | 0.1 | 0 |
| 7 | NR7/pNR8.165-2serA | $P_{tac}$NR8.165-2, serA | 7.4 | 3.3% |
| 8 | NR7/pNR8.165-4serA | $P_{tac}$NR8.165-4, serA | 9.3 | 4.6% |
| 9 | NR7/pNR8.180 | $P_{tac}$NR8.165-4, serA, tktA | 12.4 | 6.0% |

TABLE 11-continued

Synthesis of 3-dehydroshikimic acid under fermentor-controlled conditions.

| Entry | Construct | Genes | DHS$^a$ (g/L) | DHS (yield$^b$) |
|---|---|---|---|---|
| 10 | NR7/pNR8.182 | $P_{tac}$aroF$^{FBR}$, serA | 42.7 | 18% |
| 11 | NR7/pNR8.190 | $P_{75}$NR8.165-4, serA, tktA | 10.5 | 6.5% |

$^a$DHS: 3-dehydroshikimic acid.
$^b$yield is calculated as (mol of DHS)/(mol of glucose).

TABLE 12

Evolved KDPGal aloldase activities towards DAHP formation.

| | | DAHP formation assay (U$^a$/mg) | | | |
|---|---|---|---|---|---|
| Entry | Construct | 12 h | 24 h | 36 h | 48 h |
| 1 | NR7/pKP03-3serA | 0 | 0.11 | 0.02 | 0.01 |
| 3 | NR7/pNR8.172 | 0 | 0.05 | 0.05 | 0.05 |
| 5 | NR7/ST04-5serA | 0 | 0.30 | 0.25 | 0.22 |
| 8 | NR7/pNR8.165-4serA | 0 | 0.31 | 0.25 | 0.19 |
| 9 | NR7/pNR8.180 | 0 | 0.13 | 0.17 | 0.15 |
| 11 | NR7/pNR8.190 | 0 | 0.012 | 0.21 | 0.25 |

$^a$One unit of DAHP synthase catalyzes the formation of one μmol of 3-dehydroshikimate per minute at 25° C. Isopropyl β-D-thioglucopyranoside (IPTG, 23.8 mg) was added at 12 h and every 6 h after.

*E. coli* NR7/pKP03-3serA was cultured under glucose-rich conditions at 36° C., 20% air saturation and pH 7.0 in a 2.0-L working volume fermentor, 8.3 g/L of 3-dehydroshikimic acid was produced after 48 h in 5% mol/mol yield from glucose (entry 1, Table 11). In contrast, only trace amount of 3-dehydroshikimic acid was observed in fermentation broth of NR7/pNR8.074 which encoded wild-type *K. pneumoniae* dgoA and serA genes (entry 2, Table 11). *E. coli* NR7/pNR8.172 produced 5.1 g/L of 3-dehydroshikimic acid in 2.4% mol/mol yield under the same conditions (entry 3, Table 11), while NR7/pNR8.170, which encoded wild-type *E. coli* dgoA and serA genes, produced only trace amount of 3-dehydroshikimic acid (entry 4, Table 11). *E. coli* NR7/pST04-5serA produced 7.1 g/L 3-dehydroshikimic acid in 3.4% yield (entry 5, Table 11). For comparison, NR7/pNR8.121 which encoded the wild-type *S. typhimurium* dgoA gene produced a trace amount of 3-dehydroshikimic acid (entry 6, Table 11).

The evolved KDPGal aldolase specific activities toward catalyzing the condensation of pyruvate and D-erythrose 4-phosphate were measured at 12, 24, 36 and 48 h after inoculation of the culture medium in the fed-batch fermentation runs (Table 12).

With DAHP formation catalyzed by an evolved KDPGal aldolase, the first reaction in the shikimate pathway can consume the pyruvate byproduct instead of competing for the phosphoenolpyruvate substrate required by PTS-mediated glucose transport. This constitutes a fundamental departure from all previous strategies employed to increase phosphoenolpyruvate availability in microbes such as *E. coli*.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. A method for converting pyruvate and erythrose 4-phosphate (E4P) to 3-deoxy-D-arabino-heptulosonate-7-phosphate (DAHP), the method comprising contacting an isolated or recombinant 2-keto-3-deoxy-6-phosphogalactonate (KDPGal) aldolase having the amino acid sequence of SEQ ID NO:4 with a solution containing pyruvate and E4P.

2. The method of claim 1 further comprising contacting said DAHP with a 3-dehydroquinate (DHQ) synthase, thereby forming DHQ.

3. The method of claim 2 further comprising contacting said DHQ with a DHQ dehydratase, thereby forming 3-dehydroshikimate.

4. The method of claim 1, wherein said method is performed within a recombinant cell.

5. The method of claim 4, wherein said host cell was produced by transforming the cell with nucleic acid encoding at least one of a KDPGal aldolase or a DHQ synthase.

6. The method of claim 4, wherein said recombinant cell contains at least one recombinant transketolase or at least one recombinant transaldolase.

7. A method for converting pyruvate and erythrose 4-phosphate (E4P) to 3-deoxy-D-arabino-heptulosonate-7-phosphate (DAHP), comprising contacting an isolated or recombinant 2-keto-3-deoxy-6-phosphogalactonate (KDPGal) aldolase having the amino acid sequence of SEQ ID NO:4 with pyruvate and E4P, wherein said contacting converts pyruvate and E4P to DAHP.

8. The method according to claim 7, further comprising contacting DAHP with a recombinant DHQ synthase to produce DHQ from said DAHP.

9. A process for preparing 3-deoxy-D-arabino-heptulosonate-7-phosphate (DAHP), said process including the steps of:
    1) providing
        (A) erythrose 4-phosphate (E4P) and pyruvate,
        (B) an isolated or recombinant 2-keto-3-deoxy-6-phosphogalactonate (KDPGal) aldolase having the amino acid sequence of SEQ ID NO:4, and,
        (C) an aqueous medium,
    2) contacting in said medium, said KDPGal aldolase with said E4P and said pyruvate under conditions suitable for said KDPGal aldolase to catalyze the formation of 3-deoxy-D-arabino-heptulosonate-7-phosphate (DAHP) from the (E4P) and pyruvate.

10. A method for converting pyruvate and erythrose 4-phosphate (E4P) to 3-deoxy-D-arabino-heptulosonate-7-phosphate(DAHP), comprising contacting an isolated or recombinant 2-keto-3-deoxy-6-phosphogalactonate (KDPGal) aldolase having the amino acid sequence of SEQ ID NO:4 with pyruvate and E4P, wherein said contacting converts pyruvate and E4P to DAHP, wherein the recombinant KDPGal aldolase
    comprises at least one mutation selected from the group consisting of X10V, X28L, X28M, X42T, X85A, X154F, and X196I.

11. The method of claim 7, wherein said contacting step is performed in vivo in a recombinant cell.

12. The method of claim 7, further comprising obtaining recombinant KDPGal aldolase from a recombinant cell, and contacting the KDPGal aldolase with pyruvate and E4P in solution to convert pyruvate and E4P to DAHP.

13. The method of claim 7, wherein the recombinant KDPGal aldolase has a specific activity for DAHP formation in the range of 0.3 U/mg to 1.3 U/mg.

14. A method for converting pyruvate and erythrose 4-phosphate (E4P) to 3-deoxy-D-arabino-heptulosonate-7-phosphate(DAHP), comprising contacting an isolated or recombinant 2-keto-3-deoxy-6-phosphogalactonate (KDPGal) aldolase having the amino acid sequence of SEQ ID NO:4 with pyruvate and E4P, wherein said contacting converts pyruvate and E4P to DAHP, wherein the recombinant KDPGal aldolase comprises at least one mutation selected from the group consisting of X10V, X28L, X28M, X42T, X85A, X154F, and X196I, and wherein said recombinant KDPGal aldolase has higher specific activity for 3-deoxy-D-arabino-heptulosonate-7-phosphate (DAHP) formation than a native KDPGal aldolase without said at least one mutation.

15. The method of claim 14, wherein said at least one mutation is selected from the group consisting of I10V, V85A, V154F and F196I.

16. The method of claim 14, wherein the recombinant KDPGal aldolase has no mutation that is X70L.

17. The process of claim 9 further comprising recovering DAHP from said medium.

18. The process of claim 9 further comprising:
    providing a 3-dehydroquinate (DHQ) synthase, and
    contacting said DAHP with said DHQ synthase under conditions suitable for said DHQ synthase to catalyze the formation of 3-dehydroquinate from the DAHP.

19. The process of claim 18 further comprising recovering at least one of DAHP, DHQ, 3-dehydroshikimate (DHS), from said medium.

* * * * *

UNITED STATES PATENT AND TRADEMARK OFFICE
CERTIFICATE OF CORRECTION

| | |
|---|---|
| PATENT NO. | : 7,790,431 B2 |
| APPLICATION NO. | : 10/572976 |
| DATED | : September 7, 2010 |
| INVENTOR(S) | : John W. Frost |

It is certified that error appears in the above-identified patent and that said Letters Patent is hereby corrected as shown below:

In the Specification:
Column 1 Line 13 delete "This invention was made with Government support under Contract 08-R1GM065541A, awarded by the National Institutes of Health. The Government may have certain rights in this invention." and insert therefor:

--GOVERNMENT LICENSE RIGHTS

This invention was made with government support under GM065541 awarded by the National Institutes of Health. The government has certain rights in the invention.--

Signed and Sealed this
Sixth Day of May, 2014

Michelle K. Lee
*Deputy Director of the United States Patent and Trademark Office*

SEQUENCE LISTING

<160> NUMBER OF SEQ ID NOS: 34

<210> SEQ ID NO 1
<211> LENGTH: 618
<212> TYPE: DNA
<213> ORGANISM: Escherichia coli
<220> FEATURE:
<221> NAME/KEY: CDS
<222> LOCATION: (1)..(615)
<223> OTHER INFORMATION: dgoA CDS for KDPGal Aldolase

<400> SEQUENCE: 1

```
atg cag tgg caa act aaa ctc ccg ctg atc gcc att ttg cgc ggt att      48
Met Gln Trp Gln Thr Lys Leu Pro Leu Ile Ala Ile Leu Arg Gly Ile
1               5                   10                  15 acg ccc gac gag gcg ctg gcg cat gtt ggc gcg gtg att gac gcc ggg      96
Thr Pro Asp Glu Ala Leu Ala His Val Gly Ala Val Ile Asp Ala Gly
                20                  25                  30 ttc gac gcg gtt gaa atc ccg ctg aat tcc cca caa tgg gag caa agc     144
Phe Asp Ala Val Glu Ile Pro Leu Asn Ser Pro Gln Trp Glu Gln Ser
            35                  40                  45 att ccc gcc atc gtt gat gcg tac ggc gac aag gcg ttg att ggc gca     192
Ile Pro Ala Ile Val Asp Ala Tyr Gly Asp Lys Ala Leu Ile Gly Ala
        50                  55                  60 ggt acg gta ctg aaa cct gaa cag gtc gat gcg ctc gcc agg atg ggc     240
Gly Thr Val Leu Lys Pro Glu Gln Val Asp Ala Leu Ala Arg Met Gly
65                  70                  75                  80 tgt cag ctc atc gtt acg ccc aat atc cat agt gaa gtg atc cgc cgt     288
Cys Gln Leu Ile Val Thr Pro Asn Ile His Ser Glu Val Ile Arg Arg
                85                  90                  95 gcg gtg ggc tac ggc atg acc gtc tgc ccc ggc tgc gcg acg gcg acc     336
Ala Val Gly Tyr Gly Met Thr Val Cys Pro Gly Cys Ala Thr Ala Thr
                100                 105                 110 gaa gcc ttt acc gcg ctc gaa gcg ggc gcg cag gcg ctg aaa ata ttt     384
Glu Ala Phe Thr Ala Leu Glu Ala Gly Ala Gln Ala Leu Lys Ile Phe
            115                 120                 125 ccg tca tcg gct ttt ggt ccg caa tac atc aaa gcg tta aaa gcg gta     432
Pro Ser Ser Ala Phe Gly Pro Gln Tyr Ile Lys Ala Leu Lys Ala Val
        130                 135                 140 ttg cca tcg gac atc gca gtc ttt gcc gtt ggc ggc gtg acg cca gaa     480
Leu Pro Ser Asp Ile Ala Val Phe Ala Val Gly Gly Val Thr Pro Glu
145                 150                 155                 160 aac ctg gcg cag tgg ata gac gca ggt tgt gca ggg gcg ggc tta ggc     528
Asn Leu Ala Gln Trp Ile Asp Ala Gly Cys Ala Gly Ala Gly Leu Gly
                165                 170                 175 agc gat ctc tat cgc gcc ggg caa tcc gta gag cgc acc gcg cag cag     576
Ser Asp Leu Tyr Arg Ala Gly Gln Ser Val Glu Arg Thr Ala Gln Gln
            180                 185                 190 gca gca gca ttt gtt aag gcg tat cga gag gca gtg caa tga             618
Ala Ala Ala Phe Val Lys Ala Tyr Arg Glu Ala Val Gln
        195                 200                 205
```

<210> SEQ ID NO 2
<211> LENGTH: 205
<212> TYPE: PRT
<213> ORGANISM: Escherichia coli

<400> SEQUENCE: 2

```
Met Gln Trp Gln Thr Lys Leu Pro Leu Ile Ala Ile Leu Arg Gly Ile
1               5                   10                  15
```

-continued

```
Thr Pro Asp Glu Ala Leu Ala His Val Gly Ala Val Ile Asp Ala Gly
         20                  25                  30

Phe Asp Ala Val Glu Ile Pro Leu Asn Ser Pro Gln Trp Glu Gln Ser
     35                  40                  45

Ile Pro Ala Ile Val Asp Ala Tyr Gly Asp Lys Ala Leu Ile Gly Ala
 50                  55                  60

Gly Thr Val Leu Lys Pro Glu Gln Val Asp Ala Leu Ala Arg Met Gly
 65                  70                  75                  80

Cys Gln Leu Ile Val Thr Pro Asn Ile His Ser Val Ile Arg Arg
                 85                  90                  95

Ala Val Gly Tyr Gly Met Thr Val Cys Pro Gly Cys Ala Thr Ala Thr
             100                 105                 110

Glu Ala Phe Thr Ala Leu Glu Ala Gly Ala Gln Ala Leu Lys Ile Phe
         115                 120                 125

Pro Ser Ser Ala Phe Gly Pro Gln Tyr Ile Lys Ala Leu Lys Ala Val
 130                 135                 140

Leu Pro Ser Asp Ile Ala Val Phe Ala Val Gly Gly Val Thr Pro Glu
145                 150                 155                 160

Asn Leu Ala Gln Trp Ile Asp Ala Gly Cys Ala Gly Ala Gly Leu Gly
                 165                 170                 175

Ser Asp Leu Tyr Arg Ala Gly Gln Ser Val Glu Arg Thr Ala Gln Gln
             180                 185                 190

Ala Ala Ala Phe Val Lys Ala Tyr Arg Glu Ala Val Gln
         195                 200                 205

<210> SEQ ID NO 3
<211> LENGTH: 618
<212> TYPE: DNA
<213> ORGANISM: Klebsiella pneumoniae
<220> FEATURE:
<221> NAME/KEY: CDS
<222> LOCATION: (1)..(615)
<223> OTHER INFORMATION: dgoA CDS for KDPGal  Aldolase

<400> SEQUENCE: 3 atg cag tgg caa act aac ctt cca ctt atc gct atc ctg cgc ggt att        48
Met Gln Trp Gln Thr Asn Leu Pro Leu Ile Ala Ile Leu Arg Gly Ile
 1               5                  10                  15 acg cca gac gag gcg ctg gct cac gtt ggc gcc gtt atc gac gcc ggt        96
Thr Pro Asp Glu Ala Leu Ala His Val Gly Ala Val Ile Asp Ala Gly
             20                  25                  30 ttc gac gcg gtc gaa atc ccg ctg aac tcg ccg cag tgg gag aaa agt      144
Phe Asp Ala Val Glu Ile Pro Leu Asn Ser Pro Gln Trp Glu Lys Ser
         35                  40                  45 att ccg cag gtc gtc gac gct tac ggc gag cag gcg ctt atc ggc gcg      192
Ile Pro Gln Val Val Asp Ala Tyr Gly Glu Gln Ala Leu Ile Gly Ala
     50                  55                  60 ggc acg gtg ctg caa ccg gag cag gtc gac agg ctg gcg gcc atg ggc      240
Gly Thr Val Leu Gln Pro Glu Gln Val Asp Arg Leu Ala Ala Met Gly
 65                  70                  75                  80 tgt cgg ctg att gtg acg cca aac att caa ccg gaa gtg atc cgg cga      288
Cys Arg Leu Ile Val Thr Pro Asn Ile Gln Pro Glu Val Ile Arg Arg
                 85                  90                  95 gcg gtg ggt tac ggc atg acc gtg tgt cca ggc tgc gcc acc gcc agc      336
Ala Val Gly Tyr Gly Met Thr Val Cys Pro Gly Cys Ala Thr Ala Ser
             100                 105                 110 gaa gcc ttt agc gcg ctc gat gcc ggc gcg cag gcg cta aaa atc ttc      384
Glu Ala Phe Ser Ala Leu Asp Ala Gly Ala Gln Ala Leu Lys Ile Phe
         115                 120                 125
```

```
ccg tca tcg gct ttt ggc ccg gat tac atc aaa gcg ttg aaa gcc gtg    432
Pro Ser Ser Ala Phe Gly Pro Asp Tyr Ile Lys Ala Leu Lys Ala Val
    130                 135                 140 ctg ccg ccc gag gtt ccg gtc ttt gcc gtt ggc ggc gtg acg ccg gaa    480
Leu Pro Pro Glu Val Pro Val Phe Ala Val Gly Gly Val Thr Pro Glu
145                 150                 155                 160 aac ctg gcg cag tgg att aat gcc ggc tgt gtt ggg gca gga ttg ggt    528
Asn Leu Ala Gln Trp Ile Asn Ala Gly Cys Val Gly Ala Gly Leu Gly
                165                 170                 175 agc gat ctc tat cgt gcc ggc cag tcg gtt gaa cgt acc gcg cag cag    576
Ser Asp Leu Tyr Arg Ala Gly Gln Ser Val Glu Arg Thr Ala Gln Gln
            180                 185                 190 gca gcc gca ttc gta aaa gcg tat cga gag gca gtg aaa tga            618
Ala Ala Ala Phe Val Lys Ala Tyr Arg Glu Ala Val Lys
        195                 200                 205

<210> SEQ ID NO 4
<211> LENGTH: 205
<212> TYPE: PRT
<213> ORGANISM: Klebsiella pneumoniae

<400> SEQUENCE: 4

Met Gln Trp Gln Thr Asn Leu Pro Leu Ile Ala Ile Leu Arg Gly Ile
1               5                   10                  15

Thr Pro Asp Glu Ala Leu Ala His Val Gly Ala Val Ile Asp Ala Gly
                20                  25                  30

Phe Asp Ala Val Glu Ile Pro Leu Asn Ser Pro Gln Trp Glu Lys Ser
            35                  40                  45

Ile Pro Gln Val Val Asp Ala Tyr Gly Glu Gln Ala Leu Ile Gly Ala
        50                  55                  60

Gly Thr Val Leu Gln Pro Glu Gln Val Asp Arg Leu Ala Ala Met Gly
65                  70                  75                  80

Cys Arg Leu Ile Val Thr Pro Asn Ile Gln Pro Glu Val Ile Arg Arg
                85                  90                  95

Ala Val Gly Tyr Gly Met Thr Val Cys Pro Gly Cys Ala Thr Ala Ser
                100                 105                 110

Glu Ala Phe Ser Ala Leu Asp Ala Gly Ala Gln Ala Leu Lys Ile Phe
            115                 120                 125

Pro Ser Ser Ala Phe Gly Pro Asp Tyr Ile Lys Ala Leu Lys Ala Val
        130                 135                 140

Leu Pro Pro Glu Val Pro Val Phe Ala Val Gly Gly Val Thr Pro Glu
145                 150                 155                 160

Asn Leu Ala Gln Trp Ile Asn Ala Gly Cys Val Gly Ala Gly Leu Gly
                165                 170                 175

Ser Asp Leu Tyr Arg Ala Gly Gln Ser Val Glu Arg Thr Ala Gln Gln
            180                 185                 190

Ala Ala Ala Phe Val Lys Ala Tyr Arg Glu Ala Val Lys
        195                 200                 205

<210> SEQ ID NO 5
<211> LENGTH: 618
<212> TYPE: DNA
<213> ORGANISM: Salmonella typhimurium
<220> FEATURE:
<221> NAME/KEY: CDS
<222> LOCATION: (1)..(615)
<223> OTHER INFORMATION: dgoA CDS for KDPGal Aldolase

<400> SEQUENCE: 5
```

```
atg cag tgg caa act aat ctc cct ctc atc gct atc tta cgc ggt att    48
Met Gln Trp Gln Thr Asn Leu Pro Leu Ile Ala Ile Leu Arg Gly Ile
1               5                   10                  15 acg ccc gat gat gcc ctg gcg cac gtt ggc gcg gtg gtg gat gcg gga    96
Thr Pro Asp Asp Ala Leu Ala His Val Gly Ala Val Val Asp Ala Gly
                20                  25                  30 ttt gac gct ata gaa att ccg ctt aac tcc cca cag tgg gaa aaa agc   144
Phe Asp Ala Ile Glu Ile Pro Leu Asn Ser Pro Gln Trp Glu Lys Ser
            35                  40                  45 att tct tcc gtg gtg aag gcg tat ggc ggc agg gcg ctt att ggc gct   192
Ile Ser Ser Val Val Lys Ala Tyr Gly Gly Arg Ala Leu Ile Gly Ala
        50                  55                  60 ggt acc gta ctg aaa ccg gaa cag gta gac cag ctt gcc ggg atg ggc   240
Gly Thr Val Leu Lys Pro Glu Gln Val Asp Gln Leu Ala Gly Met Gly
65                  70                  75                  80 tgc aag ctg atc gtc acg ccg aat atc caa ccg gag gtg atc cgc cgg   288
Cys Lys Leu Ile Val Thr Pro Asn Ile Gln Pro Glu Val Ile Arg Arg
                85                  90                  95 gcg gtg agc tat ggc atg acc gtg tgt ccg ggc tgc gcc acg gca acg   336
Ala Val Ser Tyr Gly Met Thr Val Cys Pro Gly Cys Ala Thr Ala Thr
                100                 105                 110 gaa gcc ttt tct gcg ctg gat gca ggc gca cag gcg tta aaa att ttc   384
Glu Ala Phe Ser Ala Leu Asp Ala Gly Ala Gln Ala Leu Lys Ile Phe
            115                 120                 125 ccg tcg tcg gcg ttt ggt ccg ggc tac atc agc gcg ctg aaa gcg gta   432
Pro Ser Ser Ala Phe Gly Pro Gly Tyr Ile Ser Ala Leu Lys Ala Val
        130                 135                 140 ctt ccg ccg gat gtt ccg cta ttt gcc gtc ggc ggc gtg acg ccg gaa   480
Leu Pro Pro Asp Val Pro Leu Phe Ala Val Gly Gly Val Thr Pro Glu
145                 150                 155                 160 aac cta gcg caa tgg att aaa gca ggc tgt gtg ggc gcg gga ttg ggt   528
Asn Leu Ala Gln Trp Ile Lys Ala Gly Cys Val Gly Ala Gly Leu Gly
                165                 170                 175 agc gat ctc tat cgc gcc ggg caa tcc gtt gaa cgc acc gcg cag cag   576
Ser Asp Leu Tyr Arg Ala Gly Gln Ser Val Glu Arg Thr Ala Gln Gln
                180                 185                 190 gct gcg gca ttt gtt aat gcg tat cga gag gca gtg aaa tga           618
Ala Ala Ala Phe Val Asn Ala Tyr Arg Glu Ala Val Lys
            195                 200                 205

<210> SEQ ID NO 6
<211> LENGTH: 205
<212> TYPE: PRT
<213> ORGANISM: Salmonella typhimurium

<400> SEQUENCE: 6

Met Gln Trp Gln Thr Asn Leu Pro Leu Ile Ala Ile Leu Arg Gly Ile
1               5                   10                  15

Thr Pro Asp Asp Ala Leu Ala His Val Gly Ala Val Val Asp Ala Gly
                20                  25                  30

Phe Asp Ala Ile Glu Ile Pro Leu Asn Ser Pro Gln Trp Glu Lys Ser
            35                  40                  45

Ile Ser Ser Val Val Lys Ala Tyr Gly Gly Arg Ala Leu Ile Gly Ala
        50                  55                  60

Gly Thr Val Leu Lys Pro Glu Gln Val Asp Gln Leu Ala Gly Met Gly
65                  70                  75                  80

Cys Lys Leu Ile Val Thr Pro Asn Ile Gln Pro Glu Val Ile Arg Arg
                85                  90                  95
```

```
Ala Val Ser Tyr Gly Met Thr Val Cys Pro Gly Cys Ala Thr Ala Thr
                100                 105                 110

Glu Ala Phe Ser Ala Leu Asp Ala Gly Ala Gln Ala Leu Lys Ile Phe
            115                 120                 125

Pro Ser Ser Ala Phe Gly Pro Gly Tyr Ile Ser Ala Leu Lys Ala Val
        130                 135                 140

Leu Pro Pro Asp Val Pro Leu Phe Ala Val Gly Gly Val Thr Pro Glu
145                 150                 155                 160

Asn Leu Ala Gln Trp Ile Lys Ala Gly Cys Val Gly Ala Gly Leu Gly
                165                 170                 175

Ser Asp Leu Tyr Arg Ala Gly Gln Ser Val Glu Arg Thr Ala Gln Gln
            180                 185                 190

Ala Ala Ala Phe Val Asn Ala Tyr Arg Glu Ala Val Lys
        195                 200                 205

<210> SEQ ID NO 7
<211> LENGTH: 1089
<212> TYPE: DNA
<213> ORGANISM: Escherichia coli
<220> FEATURE:
<221> NAME/KEY: CDS
<222> LOCATION: (1)..(1086)
<223> OTHER INFORMATION: aroB CDS for DHQ Synthase

<400> SEQUENCE: 7 atg gag agg att gtc gtt act ctc ggg gaa cgt agt tac cca att acc      48
Met Glu Arg Ile Val Val Thr Leu Gly Glu Arg Ser Tyr Pro Ile Thr
1               5                   10                  15 atc gca tct ggt ttg ttt aat gaa cca gct tca ttc tta ccg ctg aaa     96
Ile Ala Ser Gly Leu Phe Asn Glu Pro Ala Ser Phe Leu Pro Leu Lys
                20                  25                  30 tcg ggc gag cag gtc atg ttg gtc acc aac gaa acc ctg gct cct ctg    144
Ser Gly Glu Gln Val Met Leu Val Thr Asn Glu Thr Leu Ala Pro Leu
            35                  40                  45 tat ctc gat aag gtc cgc ggc gta ctt gaa cag gcg ggt gtt aac gtc    192
Tyr Leu Asp Lys Val Arg Gly Val Leu Glu Gln Ala Gly Val Asn Val
        50                  55                  60 gat agc gtt atc ctc cct gac ggc gag cag tat aaa agc ctg gct gta    240
Asp Ser Val Ile Leu Pro Asp Gly Glu Gln Tyr Lys Ser Leu Ala Val
65                  70                  75                  80 ctc gat acc gtc ttt acg gcg ttg tta caa aaa ccg cat ggt cgc gat    288
Leu Asp Thr Val Phe Thr Ala Leu Leu Gln Lys Pro His Gly Arg Asp
                85                  90                  95 act acg ctg gtg gcg ctt ggc ggc ggc gta gtg ggc gat ctg acc ggc    336
Thr Thr Leu Val Ala Leu Gly Gly Gly Val Val Gly Asp Leu Thr Gly
                100                 105                 110 ttc gcg gcg gcg agt tat cag cgc ggt gtc cgt ttc att caa gtc ccg    384
Phe Ala Ala Ala Ser Tyr Gln Arg Gly Val Arg Phe Ile Gln Val Pro
            115                 120                 125 acg acg tta ctg tcg cag gtc gat tcc tcc gtt ggc ggc aaa act gcg    432
Thr Thr Leu Leu Ser Gln Val Asp Ser Ser Val Gly Gly Lys Thr Ala
        130                 135                 140 gtc aac cat ccc ctc ggt aaa aac atg att ggc gcg ttc tac caa cct    480
Val Asn His Pro Leu Gly Lys Asn Met Ile Gly Ala Phe Tyr Gln Pro
145                 150                 155                 160 gct tca gtg gtg gtg gat ctc gac tgt ctg aaa acg ctt ccc ccg cgt    528
Ala Ser Val Val Val Asp Leu Asp Cys Leu Lys Thr Leu Pro Pro Arg
                165                 170                 175 gag tta gcg tcg ggg ctg gca gaa gtc atc aaa tac ggc att att ctt    576
Glu Leu Ala Ser Gly Leu Ala Glu Val Ile Lys Tyr Gly Ile Ile Leu
```

```
                180                 185                 190
gac ggt gcg ttt ttt aac tgg ctg gaa gag aat ctg gat gcg ttg ttg      624
Asp Gly Ala Phe Phe Asn Trp Leu Glu Glu Asn Leu Asp Ala Leu Leu
        195                 200                 205 cgt ctg gac ggt ccg gca atg gcg tac tgt att cgc cgt tgt tgt gaa      672
Arg Leu Asp Gly Pro Ala Met Ala Tyr Cys Ile Arg Arg Cys Cys Glu
    210                 215                 220 ctg aag gca gaa gtt gtc gcc gcc gac gag cgc gaa acc ggg tta cgt      720
Leu Lys Ala Glu Val Val Ala Ala Asp Glu Arg Glu Thr Gly Leu Arg
225                 230                 235                 240 gct tta ctg aat ctg gga cac acc ttt ggt cat gcc att gaa gct gaa      768
Ala Leu Leu Asn Leu Gly His Thr Phe Gly His Ala Ile Glu Ala Glu
                245                 250                 255 atg ggg tat ggc aat tgg tta cat ggt gaa gcg gtc gct gcg ggt atg      816
Met Gly Tyr Gly Asn Trp Leu His Gly Glu Ala Val Ala Ala Gly Met
            260                 265                 270 gtg atg gcg gcg cgg acg tcg gaa cgt ctc ggg cag ttt agt tct gcc      864
Val Met Ala Ala Arg Thr Ser Glu Arg Leu Gly Gln Phe Ser Ser Ala
        275                 280                 285 gaa acg cag cgt att ata acc ctg ctc aag cgg gct ggg tta ccg gtc      912
Glu Thr Gln Arg Ile Ile Thr Leu Leu Lys Arg Ala Gly Leu Pro Val
    290                 295                 300 aat ggg ccg cgc gaa atg tcc gcg cag gcg tat tta ccg cat atg ctg      960
Asn Gly Pro Arg Glu Met Ser Ala Gln Ala Tyr Leu Pro His Met Leu
305                 310                 315                 320 cgt gac aag aaa gtc ctt gcg gga gag atg cgc tta att ctt ccg ttg     1008
Arg Asp Lys Lys Val Leu Ala Gly Glu Met Arg Leu Ile Leu Pro Leu
                325                 330                 335 gca att ggt aag agt gaa gtt cgc agc ggc gtt tcg cac gag ctt gtt     1056
Ala Ile Gly Lys Ser Glu Val Arg Ser Gly Val Ser His Glu Leu Val
            340                 345                 350 ctt aac gcc att gcc gat tgt caa tca gcg taa                         1089
Leu Asn Ala Ile Ala Asp Cys Gln Ser Ala
        355                 360

<210> SEQ ID NO 8
<211> LENGTH: 362
<212> TYPE: PRT
<213> ORGANISM: Escherichia coli

<400> SEQUENCE: 8

Met Glu Arg Ile Val Val Thr Leu Gly Glu Arg Ser Tyr Pro Ile Thr
1               5                   10                  15

Ile Ala Ser Gly Leu Phe Asn Glu Pro Ala Ser Phe Leu Pro Leu Lys
            20                  25                  30

Ser Gly Glu Gln Val Met Leu Val Thr Asn Glu Thr Leu Ala Pro Leu
        35                  40                  45

Tyr Leu Asp Lys Val Arg Gly Val Leu Glu Gln Ala Gly Val Asn Val
    50                  55                  60

Asp Ser Val Ile Leu Pro Asp Gly Glu Gln Tyr Lys Ser Leu Ala Val
65                  70                  75                  80

Leu Asp Thr Val Phe Thr Ala Leu Leu Gln Lys Pro His Gly Arg Asp
                85                  90                  95

Thr Thr Leu Val Ala Leu Gly Gly Gly Val Val Gly Asp Leu Thr Gly
            100                 105                 110

Phe Ala Ala Ala Ser Tyr Gln Arg Gly Val Arg Phe Ile Gln Val Pro
        115                 120                 125

Thr Thr Leu Leu Ser Gln Val Asp Ser Ser Val Gly Gly Lys Thr Ala
```

```
            130                 135                 140
Val Asn His Pro Leu Gly Lys Asn Met Ile Gly Ala Phe Tyr Gln Pro
145                 150                 155                 160

Ala Ser Val Val Asp Leu Asp Cys Leu Lys Thr Leu Pro Pro Arg
                165                 170                 175

Glu Leu Ala Ser Gly Leu Ala Glu Val Ile Lys Tyr Gly Ile Ile Leu
                180                 185                 190

Asp Gly Ala Phe Phe Asn Trp Leu Glu Glu Asn Leu Asp Ala Leu Leu
                195                 200                 205

Arg Leu Asp Gly Pro Ala Met Ala Tyr Cys Ile Arg Arg Cys Cys Glu
    210                 215                 220

Leu Lys Ala Glu Val Val Ala Ala Asp Glu Arg Glu Thr Gly Leu Arg
225                 230                 235                 240

Ala Leu Leu Asn Leu Gly His Thr Phe Gly His Ala Ile Glu Ala Glu
                245                 250                 255

Met Gly Tyr Gly Asn Trp Leu His Gly Glu Ala Val Ala Ala Gly Met
                260                 265                 270

Val Met Ala Ala Arg Thr Ser Glu Arg Leu Gly Gln Phe Ser Ser Ala
    275                 280                 285

Glu Thr Gln Arg Ile Ile Thr Leu Leu Lys Arg Ala Gly Leu Pro Val
    290                 295                 300

Asn Gly Pro Arg Glu Met Ser Ala Gln Ala Tyr Leu Pro His Met Leu
305                 310                 315                 320

Arg Asp Lys Lys Val Leu Ala Gly Glu Met Arg Leu Ile Leu Pro Leu
                325                 330                 335

Ala Ile Gly Lys Ser Glu Val Arg Ser Gly Val Ser His Glu Leu Val
                340                 345                 350

Leu Asn Ala Ile Ala Asp Cys Gln Ser Ala
                355                 360

<210> SEQ ID NO 9
<211> LENGTH: 1992
<212> TYPE: DNA
<213> ORGANISM: Escherichia coli
<220> FEATURE:
<221> NAME/KEY: CDS
<222> LOCATION: (1)..(1989)
<223> OTHER INFORMATION: tktA CDS for major Tranketolase isozyme

<400> SEQUENCE: 9 atg tcc tca cgt aaa gag ctt gcc aat gct att cgt gcg ctg agc atg        48
Met Ser Ser Arg Lys Glu Leu Ala Asn Ala Ile Arg Ala Leu Ser Met
1               5                   10                  15 gac gca gta cag aaa gcc aaa tcc ggt cac ccg ggt gcc cct atg ggt        96
Asp Ala Val Gln Lys Ala Lys Ser Gly His Pro Gly Ala Pro Met Gly
                20                  25                  30 atg gct gac att gcc gaa gtc ctg tgg cgt gat ttc ctg aaa cac aac       144
Met Ala Asp Ile Ala Glu Val Leu Trp Arg Asp Phe Leu Lys His Asn
            35                  40                  45 ccg cag aat ccg tcc tgg gct gac cgt gac cgc ttc gtg ctg tcc aac       192
Pro Gln Asn Pro Ser Trp Ala Asp Arg Asp Arg Phe Val Leu Ser Asn
        50                  55                  60 ggc cac ggc tcc atg ctg atc tac agc ctg ctg cac ctc acc ggt tac       240
Gly His Gly Ser Met Leu Ile Tyr Ser Leu Leu His Leu Thr Gly Tyr
65                  70                  75                  80 gat ctg ccg atg gaa gaa ctg aaa aac ttc cgt cag ctg cac tct aaa       288
Asp Leu Pro Met Glu Glu Leu Lys Asn Phe Arg Gln Leu His Ser Lys
                85                  90                  95
```

```
act ccg ggt cac ccg gaa gtg ggt tac acc gct ggt gtg gaa acc acc     336
Thr Pro Gly His Pro Glu Val Gly Tyr Thr Ala Gly Val Glu Thr Thr
            100                 105                 110 acc ggt ccg ctg ggt cag ggt att gcc aac gca gtc ggt atg gcg att     384
Thr Gly Pro Leu Gly Gln Gly Ile Ala Asn Ala Val Gly Met Ala Ile
        115                 120                 125 gca gaa aaa acg ctg gcg gcg cag ttt aac cgt ccg ggc cac gac att     432
Ala Glu Lys Thr Leu Ala Ala Gln Phe Asn Arg Pro Gly His Asp Ile
130                 135                 140 gtc gac cac tac acc tac gcc ttc atg ggc gac ggc tgc atg atg gaa     480
Val Asp His Tyr Thr Tyr Ala Phe Met Gly Asp Gly Cys Met Met Glu
145                 150                 155                 160 ggc atc tcc cac gaa gtt tgc tct ctg gcg ggt acg ctg aag ctg ggt     528
Gly Ile Ser His Glu Val Cys Ser Leu Ala Gly Thr Leu Lys Leu Gly
                165                 170                 175 aaa ctg att gca ttc tac gat gac aac ggt att tct atc gat ggt cac     576
Lys Leu Ile Ala Phe Tyr Asp Asp Asn Gly Ile Ser Ile Asp Gly His
            180                 185                 190 gtt gaa ggc tgg ttc acc gac gac acc gca atg cgt ttc gaa gct tac     624
Val Glu Gly Trp Phe Thr Asp Asp Thr Ala Met Arg Phe Glu Ala Tyr
        195                 200                 205 ggc tgg cac gtt att cgc gac atc gac ggt cat gac gcg gca tct atc     672
Gly Trp His Val Ile Arg Asp Ile Asp Gly His Asp Ala Ala Ser Ile
210                 215                 220 aaa cgc gca gta gaa gaa gcg cgc gca gtg act gac aaa cct tcc ctg     720
Lys Arg Ala Val Glu Glu Ala Arg Ala Val Thr Asp Lys Pro Ser Leu
225                 230                 235                 240 ctg atg tgc aaa acc atc atc ggt ttc ggt tcc ccg aac aaa gcc ggt     768
Leu Met Cys Lys Thr Ile Ile Gly Phe Gly Ser Pro Asn Lys Ala Gly
                245                 250                 255 acc cac gac tcc cac ggt gcg ccg ctg ggc gac gct gaa att gcc ctg     816
Thr His Asp Ser His Gly Ala Pro Leu Gly Asp Ala Glu Ile Ala Leu
            260                 265                 270 acc cgc gaa caa ctg ggc tgg aaa tat gcg ccg ttc gaa atc ccg tct     864
Thr Arg Glu Gln Leu Gly Trp Lys Tyr Ala Pro Phe Glu Ile Pro Ser
        275                 280                 285 gaa atc tat gct cag tgg gat gcg aaa gaa gca ggc cag gcg aaa gaa     912
Glu Ile Tyr Ala Gln Trp Asp Ala Lys Glu Ala Gly Gln Ala Lys Glu
290                 295                 300 tcc gca tgg aac gag aaa ttc gct gct tac gcg aaa gct tat ccg cag     960
Ser Ala Trp Asn Glu Lys Phe Ala Ala Tyr Ala Lys Ala Tyr Pro Gln
305                 310                 315                 320 gaa gcc gct gaa ttt acc cgc cgt atg aaa ggc gaa atg ccg tct gac    1008
Glu Ala Ala Glu Phe Thr Arg Arg Met Lys Gly Glu Met Pro Ser Asp
                325                 330                 335 ttc gac gct aaa gcg aaa gag ttc atc gct aaa ctg cag gct aat ccg    1056
Phe Asp Ala Lys Ala Lys Glu Phe Ile Ala Lys Leu Gln Ala Asn Pro
            340                 345                 350 gcg aaa atc gcc agc cgt aaa gcg tct cag aat gct atc gaa gcg ttc    1104
Ala Lys Ile Ala Ser Arg Lys Ala Ser Gln Asn Ala Ile Glu Ala Phe
        355                 360                 365 ggt ccg ctg ttg ccg gaa ttc ctc ggc ggt tct gct gac ctg gcg ccg    1152
Gly Pro Leu Leu Pro Glu Phe Leu Gly Gly Ser Ala Asp Leu Ala Pro
370                 375                 380 tct aac ctg acc ctg tgg tct ggt tct aaa gca atc aac gaa gat gct    1200
Ser Asn Leu Thr Leu Trp Ser Gly Ser Lys Ala Ile Asn Glu Asp Ala
385                 390                 395                 400 gcg ggt aac tac atc cac tac ggt gtt cgc gag ttc ggt atg acc gcg    1248
Ala Gly Asn Tyr Ile His Tyr Gly Val Arg Glu Phe Gly Met Thr Ala
```

-continued

```
                405                 410                 415
att gct aac ggt atc tcc ctg cac ggt ggc ttc ctg ccg tac acc tcc      1296
Ile Ala Asn Gly Ile Ser Leu His Gly Gly Phe Leu Pro Tyr Thr Ser
            420                 425                 430 acc ttc ctg atg ttc gtg gaa tac gca cgt aac gcc gta cgt atg gct      1344
Thr Phe Leu Met Phe Val Glu Tyr Ala Arg Asn Ala Val Arg Met Ala
        435                 440                 445 gcg ctg atg aaa cag cgt cag gtg atg gtt tac acc cac gac tcc atc      1392
Ala Leu Met Lys Gln Arg Gln Val Met Val Tyr Thr His Asp Ser Ile
    450                 455                 460 ggt ctg ggc gaa gac ggg ccg act cac cag ccg gtt gag cag gtc gct      1440
Gly Leu Gly Glu Asp Gly Pro Thr His Gln Pro Val Glu Gln Val Ala
465                 470                 475                 480 tct ctg cgc gta acc ccg aac atg tct aca tgg cgt ccg tgt gac cag      1488
Ser Leu Arg Val Thr Pro Asn Met Ser Thr Trp Arg Pro Cys Asp Gln
                485                 490                 495 gtt gaa tcc gcg gtc gcg tgg aaa tac ggt gtt gag cgt cag gac ggc      1536
Val Glu Ser Ala Val Ala Trp Lys Tyr Gly Val Glu Arg Gln Asp Gly
            500                 505                 510 ccg acc gca ctg atc ctc tcc cgt cag aac ctg gcg cag cag gaa cga      1584
Pro Thr Ala Leu Ile Leu Ser Arg Gln Asn Leu Ala Gln Gln Glu Arg
        515                 520                 525 act gaa gag caa ctg gca aac atc gcg cgc ggt ggt tat gtc ctg aaa      1632
Thr Glu Glu Gln Leu Ala Asn Ile Ala Arg Gly Gly Tyr Val Leu Lys
    530                 535                 540 gac tgc gcc ggt cag ccg gaa ctg att ttc atc gct acc ggt tca gaa      1680
Asp Cys Ala Gly Gln Pro Glu Leu Ile Phe Ile Ala Thr Gly Ser Glu
545                 550                 555                 560 gtt gaa ctg gct gtt gct gcc tac gaa aaa ctg act gcc gaa ggc gtg      1728
Val Glu Leu Ala Val Ala Ala Tyr Glu Lys Leu Thr Ala Glu Gly Val
                565                 570                 575 aaa gcg cgc gtg gtg tcc atg tcg tct acc gac gca ttt gac aag cag      1776
Lys Ala Arg Val Val Ser Met Ser Ser Thr Asp Ala Phe Asp Lys Gln
            580                 585                 590 gat gct gct tac cgt gaa tcc gta ctg ccg aaa gcg gtt act gca cgc      1824
Asp Ala Ala Tyr Arg Glu Ser Val Leu Pro Lys Ala Val Thr Ala Arg
        595                 600                 605 gtt gct gta gaa gcg ggt att gct gac tac tgg tac aag tat gtt ggc      1872
Val Ala Val Glu Ala Gly Ile Ala Asp Tyr Trp Tyr Lys Tyr Val Gly
    610                 615                 620 ctg aac ggt gct atc gtc ggt atg acc acc ttc ggt gaa tct gct ccg      1920
Leu Asn Gly Ala Ile Val Gly Met Thr Thr Phe Gly Glu Ser Ala Pro
625                 630                 635                 640 gca gag ctg ctg ttt gaa gag ttc ggc ttc act gtt gat aac gtt gtt      1968
Ala Glu Leu Leu Phe Glu Glu Phe Gly Phe Thr Val Asp Asn Val Val
                645                 650                 655 gcg aaa gca aaa gaa ctg ctg taa                                      1992
Ala Lys Ala Lys Glu Leu Leu
            660
```

<210> SEQ ID NO 10
<211> LENGTH: 663
<212> TYPE: PRT
<213> ORGANISM: Escherichia coli

<400> SEQUENCE: 10

```
Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30
```

-continued

```
Met Ala Asp Ile Ala Glu Val Leu Trp Arg Asp Phe Leu Lys His Asn
            35                  40                  45

Pro Gln Asn Pro Ser Trp Ala Asp Arg Asp Arg Phe Val Leu Ser Asn
 50                  55                  60

Gly His Gly Ser Met Leu Ile Tyr Ser Leu Leu His Leu Thr Gly Tyr
 65                  70                  75                  80

Asp Leu Pro Met Glu Glu Leu Lys Asn Phe Arg Gln Leu His Ser Lys
                     85                  90                  95

Thr Pro Gly His Pro Glu Val Gly Tyr Thr Ala Gly Val Glu Thr Thr
                100                 105                 110

Thr Gly Pro Leu Gly Gln Gly Ile Ala Asn Ala Val Gly Met Ala Ile
            115                 120                 125

Ala Glu Lys Thr Leu Ala Ala Gln Phe Asn Arg Pro Gly His Asp Ile
        130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Asp Thr Ala Met Arg Phe Glu Ala Tyr
        195                 200                 205

Gly Trp His Val Ile Arg Asp Ile Asp Gly His Asp Ala Ala Ser Ile
    210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
        355                 360                 365

Gly Pro Leu Leu Pro Glu Phe Leu Gly Gly Ser Ala Asp Leu Ala Pro
    370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445
```

-continued

```
Ala Leu Met Lys Gln Arg Gln Val Met Val Tyr Thr His Asp Ser Ile
    450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

Thr Glu Glu Gln Leu Ala Asn Ile Ala Arg Gly Gly Tyr Val Leu Lys
530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Ser Ser Thr Asp Ala Phe Asp Lys Gln
            580                 585                 590

Asp Ala Ala Tyr Arg Glu Ser Val Leu Pro Lys Ala Val Thr Ala Arg
        595                 600                 605

Val Ala Val Glu Ala Gly Ile Ala Asp Tyr Trp Tyr Lys Tyr Val Gly
610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
                645                 650                 655

Ala Lys Ala Lys Glu Leu Leu
            660

<210> SEQ ID NO 11
<211> LENGTH: 2004
<212> TYPE: DNA
<213> ORGANISM: Escherichia coli
<220> FEATURE:
<221> NAME/KEY: CDS
<222> LOCATION: (1)..(2001)
<223> OTHER INFORMATION: tktB CDS for minor Transketolase isozyme

<400> SEQUENCE: 11 atg tcc cga aaa gac ctt gcc aat gcg att cgc gca ctc agt atg gat     48
Met Ser Arg Lys Asp Leu Ala Asn Ala Ile Arg Ala Leu Ser Met Asp
1               5                   10                  15 gcg gta caa aaa gcc aac tct ggt cat ccc ggc gcg ccg atg ggc atg     96
Ala Val Gln Lys Ala Asn Ser Gly His Pro Gly Ala Pro Met Gly Met
            20                  25                  30 gct gat att gcc gaa gtg ctg tgg aac gat ttt ctt aaa cat aac cct    144
Ala Asp Ile Ala Glu Val Leu Trp Asn Asp Phe Leu Lys His Asn Pro
        35                  40                  45 acc gac cca acc tgg tat gat cgc gac cgc ttt att ctt tcc aac ggt    192
Thr Asp Pro Thr Trp Tyr Asp Arg Asp Arg Phe Ile Leu Ser Asn Gly
    50                  55                  60 cac gcg tcg atg ctg ctc tac agt ttg cta cat ctg acc ggt tac gac    240
His Ala Ser Met Leu Leu Tyr Ser Leu Leu His Leu Thr Gly Tyr Asp
65                  70                  75                  80 ctg ccg ctg gaa gaa ctg aag aac ttc cgt cag ttg cat tcg aaa acc    288
Leu Pro Leu Glu Glu Leu Lys Asn Phe Arg Gln Leu His Ser Lys Thr
                85                  90                  95 cca ggc cac ccg gag att ggc tat acg cca ggc gtt gaa acc acc acc    336
```

|  |  |  |  |  |  |  |  |  |  |  |  |  |  |  |  |
|--|--|--|--|--|--|--|--|--|--|--|--|--|--|--|--|
| Pro | Gly | His | Pro | Glu | Ile | Gly | Tyr | Thr | Pro | Gly | Val | Glu | Thr | Thr | Thr |
|  |  |  | 100 |  |  |  | 105 |  |  |  | 110 |  |  |  |  |

```
ggc ccg ctt gga caa ggt ttg gcg aac gcc gtc ggg ctg gcg ata gca      384
Gly Pro Leu Gly Gln Gly Leu Ala Asn Ala Val Gly Leu Ala Ile Ala
        115                 120                 125 gag cgt aca ctg gcg gcg cag ttt aac cag cca gac cat gag atc gtc      432
Glu Arg Thr Leu Ala Ala Gln Phe Asn Gln Pro Asp His Glu Ile Val
130                 135                 140 gat cac ttc acc tat gtg ttt atg ggc gac ggc tgc ctg atg gaa ggt      480
Asp His Phe Thr Tyr Val Phe Met Gly Asp Gly Cys Leu Met Glu Gly
145                 150                 155                 160 att tcc cac gaa gtc tgt tcg ctg gca ggc acg ctg gga ctg ggc aag      528
Ile Ser His Glu Val Cys Ser Leu Ala Gly Thr Leu Gly Leu Gly Lys
                165                 170                 175 ctg att ggt ttt tac gat cac aac ggt att tcc atc gac ggt gaa aca      576
Leu Ile Gly Phe Tyr Asp His Asn Gly Ile Ser Ile Asp Gly Glu Thr
            180                 185                 190 gaa ggc tgg ttt acc gac gat acg gca aaa cgt ttt gaa gcc tat cac      624
Glu Gly Trp Phe Thr Asp Asp Thr Ala Lys Arg Phe Glu Ala Tyr His
        195                 200                 205 tgg cat gtg atc cat gaa atc gac ggt cac gat ccg cag gcg gtg aag      672
Trp His Val Ile His Glu Ile Asp Gly His Asp Pro Gln Ala Val Lys
210                 215                 220 gaa gcg atc ctt gaa gcg caa agc gtg aaa gat aag ccg tcg ctg att      720
Glu Ala Ile Leu Glu Ala Gln Ser Val Lys Asp Lys Pro Ser Leu Ile
225                 230                 235                 240 atc tgc cgt acg gtg att ggc ttt ggt tcg ccg aat aaa gca ggt aag      768
Ile Cys Arg Thr Val Ile Gly Phe Gly Ser Pro Asn Lys Ala Gly Lys
                245                 250                 255 gaa gag gcg cac ggc gca cca ctg ggg gaa gaa gaa gtg gcg ctg gca      816
Glu Glu Ala His Gly Ala Pro Leu Gly Glu Glu Glu Val Ala Leu Ala
            260                 265                 270 cgg caa aaa ctg ggc tgg cac cat ccg cca ttt gag atc cct aaa gag      864
Arg Gln Lys Leu Gly Trp His His Pro Pro Phe Glu Ile Pro Lys Glu
        275                 280                 285 att tat cac gcc tgg gat gcc cgt gaa aaa ggc gaa aaa gcg cag cag      912
Ile Tyr His Ala Trp Asp Ala Arg Glu Lys Gly Glu Lys Ala Gln Gln
290                 295                 300 agc tgg aat gag aag ttt gcc gcc tat aaa aag gct cat ccg caa ctg      960
Ser Trp Asn Glu Lys Phe Ala Ala Tyr Lys Lys Ala His Pro Gln Leu
305                 310                 315                 320 gca gaa gag ttt acc cga cgg atg agc ggt ggt tta ccg aag gac tgg     1008
Ala Glu Glu Phe Thr Arg Arg Met Ser Gly Gly Leu Pro Lys Asp Trp
                325                 330                 335 gag aaa acg act cag aaa tat atc aat gag tta cag gca aat ccg gcg     1056
Glu Lys Thr Thr Gln Lys Tyr Ile Asn Glu Leu Gln Ala Asn Pro Ala
            340                 345                 350 aaa atc gct acc cgt aag gct tcg caa aat acg ctt aac gct tac ggg     1104
Lys Ile Ala Thr Arg Lys Ala Ser Gln Asn Thr Leu Asn Ala Tyr Gly
        355                 360                 365 ccg atg ctg cct gag ttg ctc ggc ggt tcg gcg gat ctg gct ccc agc     1152
Pro Met Leu Pro Glu Leu Leu Gly Gly Ser Ala Asp Leu Ala Pro Ser
370                 375                 380 aac ctg acc atc tgg aaa ggt tct gtt tcg ctg aag gaa gat cca gcg     1200
Asn Leu Thr Ile Trp Lys Gly Ser Val Ser Leu Lys Glu Asp Pro Ala
385                 390                 395                 400 ggc aac tac att cac tac ggg gtg cgt gaa ttt ggc atg acc gct atc     1248
Gly Asn Tyr Ile His Tyr Gly Val Arg Glu Phe Gly Met Thr Ala Ile
                405                 410                 415
```

-continued

```
gcc aac ggc atc gcg cac cac ggc ggc ttt gtg ccg tat acc gcg acg        1296
Ala Asn Gly Ile Ala His His Gly Gly Phe Val Pro Tyr Thr Ala Thr
            420                 425                 430 ttc ctg atg ttt gtt gaa tac gcc cgt aac gcc gcg cgg atg gcg gca        1344
Phe Leu Met Phe Val Glu Tyr Ala Arg Asn Ala Ala Arg Met Ala Ala
        435                 440                 445 ctg atg aaa gcg cgg cag att atg gtt tat acc cac gac tca att ggc        1392
Leu Met Lys Ala Arg Gln Ile Met Val Tyr Thr His Asp Ser Ile Gly
    450                 455                 460 ctg ggc gaa gat ggt ccg acg cac cag gct gtt gag caa ctg gcc agc        1440
Leu Gly Glu Asp Gly Pro Thr His Gln Ala Val Glu Gln Leu Ala Ser
465                 470                 475                 480 ctg cgc tta acg cca aat ttc agc acc tgg cga ccg tgc gat cag gtg        1488
Leu Arg Leu Thr Pro Asn Phe Ser Thr Trp Arg Pro Cys Asp Gln Val
                485                 490                 495 gaa gcg gcg gtg ggc tgg aag ctg gcg gtt gag cgc cac aac gga ccg        1536
Glu Ala Ala Val Gly Trp Lys Leu Ala Val Glu Arg His Asn Gly Pro
            500                 505                 510 acg gca ctg atc ctc tca agg cag aat ctg gcc cag gtg gaa cgt acg        1584
Thr Ala Leu Ile Leu Ser Arg Gln Asn Leu Ala Gln Val Glu Arg Thr
        515                 520                 525 ccg gat cag gtt aaa gag att gct cgt ggc ggt tat gtg ctg aaa gac        1632
Pro Asp Gln Val Lys Glu Ile Ala Arg Gly Gly Tyr Val Leu Lys Asp
    530                 535                 540 agc ggc ggt aag cca gat att att ctg att gcc acc ggt tca gag atg        1680
Ser Gly Gly Lys Pro Asp Ile Ile Leu Ile Ala Thr Gly Ser Glu Met
545                 550                 555                 560 gaa att acc ctg caa gcg gca gag aaa tta gca gga gaa ggt cgc aat        1728
Glu Ile Thr Leu Gln Ala Ala Glu Lys Leu Ala Gly Glu Gly Arg Asn
                565                 570                 575 gta cgc gta gtt tcc ctg ccc tcg acc gat att ttc gac gcc cag gat        1776
Val Arg Val Val Ser Leu Pro Ser Thr Asp Ile Phe Asp Ala Gln Asp
            580                 585                 590 gag gaa tat cgg gag tcg gtg ttg cct tct aac gtt gcg gct cgc gtg        1824
Glu Glu Tyr Arg Glu Ser Val Leu Pro Ser Asn Val Ala Ala Arg Val
        595                 600                 605 gcg gtg gaa gca ggt att gcc gat tac tgg tac aag tat gtt ggt ctg        1872
Ala Val Glu Ala Gly Ile Ala Asp Tyr Trp Tyr Lys Tyr Val Gly Leu
    610                 615                 620 aaa ggg gca att gtc ggg atg acg ggt tac ggg gaa tct gct ccg gcg        1920
Lys Gly Ala Ile Val Gly Met Thr Gly Tyr Gly Glu Ser Ala Pro Ala
625                 630                 635                 640 gat aag ctg ttc ccg ttc ttt ggc ttt acc gcc gag aat att gtg gca        1968
Asp Lys Leu Phe Pro Phe Phe Gly Phe Thr Ala Glu Asn Ile Val Ala
                645                 650                 655 aaa gcg cat aag gtg ctg gga gtg aaa ggt gcc tga                        2004
Lys Ala His Lys Val Leu Gly Val Lys Gly Ala
            660                 665
```

<210> SEQ ID NO 12
<211> LENGTH: 667
<212> TYPE: PRT
<213> ORGANISM: Escherichia coli

<400> SEQUENCE: 12

```
Met Ser Arg Lys Asp Leu Ala Asn Ala Ile Arg Ala Leu Ser Met Asp
1               5                   10                  15

Ala Val Gln Lys Ala Asn Ser Gly His Pro Gly Ala Pro Met Gly Met
            20                  25                  30

Ala Asp Ile Ala Glu Val Leu Trp Asn Asp Phe Leu Lys His Asn Pro
```

```
                35                  40                  45
Thr Asp Pro Thr Trp Tyr Asp Arg Asp Arg Phe Ile Leu Ser Asn Gly
 50                  55                  60

His Ala Ser Met Leu Leu Tyr Ser Leu Leu His Leu Thr Gly Tyr Asp
 65                  70                  75                  80

Leu Pro Leu Glu Glu Leu Lys Asn Phe Arg Gln Leu His Ser Lys Thr
                 85                  90                  95

Pro Gly His Pro Glu Ile Gly Tyr Thr Pro Gly Val Glu Thr Thr Thr
                100                 105                 110

Gly Pro Leu Gly Gln Gly Leu Ala Asn Ala Val Gly Leu Ala Ile Ala
            115                 120                 125

Glu Arg Thr Leu Ala Ala Gln Phe Asn Gln Pro Asp His Glu Ile Val
130                 135                 140

Asp His Phe Thr Tyr Val Phe Met Gly Asp Gly Cys Leu Met Glu Gly
145                 150                 155                 160

Ile Ser His Glu Val Cys Ser Leu Ala Gly Thr Leu Gly Leu Gly Lys
                165                 170                 175

Leu Ile Gly Phe Tyr Asp His Asn Gly Ile Ser Ile Asp Gly Glu Thr
            180                 185                 190

Glu Gly Trp Phe Thr Asp Asp Thr Ala Lys Arg Phe Glu Ala Tyr His
            195                 200                 205

Trp His Val Ile His Glu Ile Asp Gly His Asp Pro Gln Ala Val Lys
210                 215                 220

Glu Ala Ile Leu Glu Ala Gln Ser Val Lys Asp Lys Pro Ser Leu Ile
225                 230                 235                 240

Ile Cys Arg Thr Val Ile Gly Phe Gly Ser Pro Asn Lys Ala Gly Lys
                245                 250                 255

Glu Glu Ala His Gly Ala Pro Leu Gly Glu Glu Val Ala Leu Ala
            260                 265                 270

Arg Gln Lys Leu Gly Trp His His Pro Pro Phe Glu Ile Pro Lys Glu
            275                 280                 285

Ile Tyr His Ala Trp Asp Ala Arg Glu Lys Gly Glu Lys Ala Gln Gln
290                 295                 300

Ser Trp Asn Glu Lys Phe Ala Ala Tyr Lys Lys Ala His Pro Gln Leu
305                 310                 315                 320

Ala Glu Glu Phe Thr Arg Arg Met Ser Gly Gly Leu Pro Lys Asp Trp
                325                 330                 335

Glu Lys Thr Thr Gln Lys Tyr Ile Asn Glu Leu Gln Ala Asn Pro Ala
            340                 345                 350

Lys Ile Ala Thr Arg Lys Ala Ser Gln Asn Thr Leu Asn Ala Tyr Gly
            355                 360                 365

Pro Met Leu Pro Glu Leu Leu Gly Gly Ser Ala Asp Leu Ala Pro Ser
370                 375                 380

Asn Leu Thr Ile Trp Lys Gly Ser Val Ser Leu Lys Glu Asp Pro Ala
385                 390                 395                 400

Gly Asn Tyr Ile His Tyr Gly Val Arg Glu Phe Gly Met Thr Ala Ile
                405                 410                 415

Ala Asn Gly Ile Ala His His Gly Gly Phe Val Pro Tyr Thr Ala Thr
            420                 425                 430

Phe Leu Met Phe Val Glu Tyr Ala Arg Asn Ala Ala Arg Met Ala Ala
            435                 440                 445

Leu Met Lys Ala Arg Gln Ile Met Val Tyr Thr His Asp Ser Ile Gly
450                 455                 460
```

```
Leu Gly Glu Asp Gly Pro Thr His Gln Ala Val Glu Gln Leu Ala Ser
465                 470                 475                 480

Leu Arg Leu Thr Pro Asn Phe Ser Thr Trp Arg Pro Cys Asp Gln Val
                485                 490                 495

Glu Ala Ala Val Gly Trp Lys Leu Ala Val Glu Arg His Asn Gly Pro
            500                 505                 510

Thr Ala Leu Ile Leu Ser Arg Gln Asn Leu Ala Gln Val Glu Arg Thr
        515                 520                 525

Pro Asp Gln Val Lys Glu Ile Ala Arg Gly Gly Tyr Val Leu Lys Asp
    530                 535                 540

Ser Gly Gly Lys Pro Asp Ile Ile Leu Ile Ala Thr Gly Ser Glu Met
545                 550                 555                 560

Glu Ile Thr Leu Gln Ala Ala Glu Lys Leu Ala Gly Glu Gly Arg Asn
                565                 570                 575

Val Arg Val Val Ser Leu Pro Ser Thr Asp Ile Phe Asp Ala Gln Asp
            580                 585                 590

Glu Glu Tyr Arg Glu Ser Val Leu Pro Ser Asn Val Ala Ala Arg Val
        595                 600                 605

Ala Val Glu Ala Gly Ile Ala Asp Tyr Trp Tyr Lys Tyr Val Gly Leu
    610                 615                 620

Lys Gly Ala Ile Val Gly Met Thr Gly Tyr Gly Glu Ser Ala Pro Ala
625                 630                 635                 640

Asp Lys Leu Phe Pro Phe Phe Gly Phe Thr Ala Glu Asn Ile Val Ala
                645                 650                 655

Lys Ala His Lys Val Leu Gly Val Lys Gly Ala
            660                 665

<210> SEQ ID NO 13
<211> LENGTH: 27
<212> TYPE: DNA
<213> ORGANISM: Artificial
<220> FEATURE:
<223> OTHER INFORMATION: Primer JWF 430

<400> SEQUENCE: 13
gctctagatg cagtggcaaa ctaaact                                         27

<210> SEQ ID NO 14
<211> LENGTH: 29
<212> TYPE: DNA
<213> ORGANISM: Artificial
<220> FEATURE:
<223> OTHER INFORMATION: Primer JWF 449

<400> SEQUENCE: 14
tagctctccg tcacgttact agatctcag                                       29

<210> SEQ ID NO 15
<211> LENGTH: 29
<212> TYPE: DNA
<213> ORGANISM: Artificial
<220> FEATURE:
<223> OTHER INFORMATION: Primer JWF 484

<400> SEQUENCE: 15
gacggatcct ataaggagca tcgctcatg                                       29

<210> SEQ ID NO 16
<211> LENGTH: 30
```

-continued

<212> TYPE: DNA
<213> ORGANISM: Artificial
<220> FEATURE:
<223> OTHER INFORMATION: Primer JWF 529

<400> SEQUENCE: 16
tagctctccg tcacgttact gacgtcgaag                                   30

<210> SEQ ID NO 17
<211> LENGTH: 20
<212> TYPE: DNA
<213> ORGANISM: Artificial
<220> FEATURE:
<223> OTHER INFORMATION: Primer JWF 501

<400> SEQUENCE: 17
gacaggaata aggagcatcg                                              20

<210> SEQ ID NO 18
<211> LENGTH: 20
<212> TYPE: DNA
<213> ORGANISM: Artificial
<220> FEATURE:
<223> OTHER INFORMATION: Primer JWF 499

<400> SEQUENCE: 18
ggaggtaaac ggtacgtggt                                              20

<210> SEQ ID NO 19
<211> LENGTH: 28
<212> TYPE: DNA
<213> ORGANISM: Artificial
<220> FEATURE:
<223> OTHER INFORMATION: Primer JWF 541

<400> SEQUENCE: 19
ggaattcgca taaacaggat cgccatca                                     28

<210> SEQ ID NO 20
<211> LENGTH: 26
<212> TYPE: DNA
<213> ORGANISM: Artificial
<220> FEATURE:
<223> OTHER INFORMATION: Primer JWF 542

<400> SEQUENCE: 20
ctggatcctt aagccacgcg agccgt                                       26

<210> SEQ ID NO 21
<211> LENGTH: 29
<212> TYPE: DNA
<213> ORGANISM: Artificial
<220> FEATURE:
<223> OTHER INFORMATION: Primer JWF 610

<400> SEQUENCE: 21
gtggatcctt aatccgttca tagtgtaaa                                    29

<210> SEQ ID NO 22
<211> LENGTH: 27
<212> TYPE: DNA
<213> ORGANISM: Artificial
<220> FEATURE:
<223> OTHER INFORMATION: Primer JWF 611

<400> SEQUENCE: 22
tgggatccat gagaaagccg actgcaa                                    27

<210> SEQ ID NO 23
<211> LENGTH: 20
<212> TYPE: DNA
<213> ORGANISM: Artificial
<220> FEATURE:
<223> OTHER INFORMATION: Primer JWF 625

<400> SEQUENCE: 23
gttcgtcagt gcaggatgga                                            20

<210> SEQ ID NO 24
<211> LENGTH: 22
<212> TYPE: DNA
<213> ORGANISM: Artificial
<220> FEATURE:
<223> OTHER INFORMATION: Primer JWF 626

<400> SEQUENCE: 24
gttcaggcgt gagttttctg ct                                         22

<210> SEQ ID NO 25
<211> LENGTH: 28
<212> TYPE: DNA
<213> ORGANISM: Artificial
<220> FEATURE:
<223> OTHER INFORMATION: Primer JWF 541

<400> SEQUENCE: 25
ggaattcgca taaacaggat cgccatca                                   28

<210> SEQ ID NO 26
<211> LENGTH: 26
<212> TYPE: DNA
<213> ORGANISM: Artificial
<220> FEATURE:
<223> OTHER INFORMATION: Primer JWF 542

<400> SEQUENCE: 26
ctggatcctt aagccacgcg agccgt                                     26

<210> SEQ ID NO 27
<211> LENGTH: 21
<212> TYPE: DNA
<213> ORGANISM: Artificial
<220> FEATURE:
<223> OTHER INFORMATION: Primer JWF 636

<400> SEQUENCE: 27
tccgtactgc gcgtattgag a                                          21

<210> SEQ ID NO 28
<211> LENGTH: 20
<212> TYPE: DNA
<213> ORGANISM: Artificial
<220> FEATURE:
<223> OTHER INFORMATION: Primer JWF 637

<400> SEQUENCE: 28
agaggcgagt ttttcgacca                                            20

<210> SEQ ID NO 29
<211> LENGTH: 20
<212> TYPE: DNA
<213> ORGANISM: Artificial

```
<220> FEATURE:
<223> OTHER INFORMATION: Primer JWF 669

<400> SEQUENCE: 29
gcagcattgt gccgccagaa                                              20

<210> SEQ ID NO 30
<211> LENGTH: 20
<212> TYPE: DNA
<213> ORGANISM: Artificial
<220> FEATURE:
<223> OTHER INFORMATION: Primer JWF 670

<400> SEQUENCE: 30
gtgcgctggt gaaatatctt                                              20

<210> SEQ ID NO 31
<211> LENGTH: 27
<212> TYPE: DNA
<213> ORGANISM: Artificial
<220> FEATURE:
<223> OTHER INFORMATION: Primer JWF 599

<400> SEQUENCE: 31
ggaattcgac aggaataagg agcatcg                                      27

<210> SEQ ID NO 32
<211> LENGTH: 29
<212> TYPE: DNA
<213> ORGANISM: Artificial
<220> FEATURE:
<223> OTHER INFORMATION: Primer JWF 560

<400> SEQUENCE: 32
gacggatcct catttcactg cctctcgat                                    29

<210> SEQ ID NO 33
<211> LENGTH: 29
<212> TYPE: DNA
<213> ORGANISM: Artificial
<220> FEATURE:
<223> OTHER INFORMATION: Primer JWF 484

<400> SEQUENCE: 33
gacggatcct ataaggagca tcgctcatg                                    29

<210> SEQ ID NO 34
<211> LENGTH: 30
<212> TYPE: DNA
<213> ORGANISM: Artificial
<220> FEATURE:
<223> OTHER INFORMATION: Primer JWF 529

<400> SEQUENCE: 34
tagctctccg tcacgttact gacgtcgaag                                   30
```